US011468761B1

(12) United States Patent
Antar et al.

(10) Patent No.: US 11,468,761 B1
(45) Date of Patent: Oct. 11, 2022

(54) HEAT-NOT-BURN ACTIVITY DETECTION DEVICE, SYSTEM AND METHOD

(71) Applicant: Halo Smart Solutions, Inc., Bay Shore, NY (US)

(72) Inventors: David Antar, Babylon, NY (US); Frank L. Jacovino, Northport, NY (US); Paul Galburt, Punta Gorda, FL (US); John B. Plunkett, Port Washington, NY (US)

(73) Assignee: Halo Smart Solutions, Inc., Bay Shore, NY (US)

( * ) Notice: Subject to any disclaimer, the term of this patent is extended or adjusted under 35 U.S.C. 154(b) by 0 days.

(21) Appl. No.: 17/715,362

(22) Filed: Apr. 7, 2022

Related U.S. Application Data

(63) Continuation of application No. 17/481,615, filed on Sep. 22, 2021, now Pat. No. 11,302,174.

(51) Int. Cl.
| | |
|---|---|
| G08B 21/00 | (2006.01) |
| G08B 21/18 | (2006.01) |
| H04N 7/18 | (2006.01) |
| G01N 33/00 | (2006.01) |

(52) U.S. Cl.
CPC ....... *G08B 21/182* (2013.01); *G01N 33/0063* (2013.01); *H04N 7/183* (2013.01); *H04N 7/188* (2013.01); *G01N 33/004* (2013.01); *G01N 33/0047* (2013.01); *G01N 33/0054* (2013.01)

(58) Field of Classification Search
CPC ............. G08B 21/182; G01N 33/0063; G01N 33/004; G01N 33/0047; G01N 33/0054; H04N 7/183; H04N 7/188
See application file for complete search history.

(56) References Cited

U.S. PATENT DOCUMENTS

| | | | |
|---|---|---|---|
| 9,933,790 B2 * | 4/2018 | Blackley | G01N 33/0036 |
| 2013/0174646 A1 * | 7/2013 | Martin | F24F 11/62 |
| | | | 73/31.02 |
| 2015/0052975 A1 * | 2/2015 | Martin | F24F 11/30 |
| | | | 73/31.02 |

* cited by examiner

*Primary Examiner* — Toan N Pham
(74) *Attorney, Agent, or Firm* — Williams Mullen; Thomas F. Bergert

(57) ABSTRACT

A sensor device, system and method can generate a profile of one or more detected substances in an environment, receive monitoring data from one or more of a group of sensors, and assess whether a heat-not-burn device activity event has been detected. In various embodiments, the sensor device includes a particle detection sensor and a gas detection sensor and a profile for heat-not-burn device activity is established with a threshold of detected particles and/or gases. In various embodiments, the profile for heat-not-burn activity is established with a threshold of gases that is not to be met or exceeded in order to generate a positive heat-not-burn detection.

20 Claims, 23 Drawing Sheets

Fig. 11

| Event Identifier | Email Set | Email Reset | VMS Set | VMS Reset | Relay 1 | Relay 2 | LED Color | LED Pattern | LED Priority | Sound |
|---|---|---|---|---|---|---|---|---|---|---|
| Ammonia | X | ☐ | ☐ | ☐ | --- | --- | --- | Steady | High | --- |
| CO | X | ☐ | ☐ | ☐ | --- | --- | --- | Steady | High | --- |
| CO2 | X | ☐ | ☐ | ☐ | --- | --- | --- | Steady | High | --- |
| Sound | X | ☐ | ☐ | ☐ | --- | --- | --- | Steady | High | --- |
| Vandal | X | ☐ | ☐ | ☐ | --- | --- | Red | 1 Sec Blink | High | Siren-Euro.wav |
| Vape | X | ☐ | ☐ | ☐ | --- | --- | --- | Steady | High | --- |
| VOC | X | ☐ | ☐ | ☐ | --- | --- | --- | Steady | High | --- |

[Save]

Speaker Volume: 120    0 (off) to 127 (max)

[Choose file] [No file chosen] [Upload Wavefile]
[--File to Delete--▼] [Delete Wavefile]

Tabs: Live View | Sensors Events | Actions Notifications | Device

Labels: 502, 602, 603, 604

506

605

| Live View | Sensors Events Actions Notifications | | Device | | |
|---|---|---|---|---|---|
| Events | | | | | |
| Event Identifier | Data Source | Threshold | Advanced | Actions | |
| Ammonia | Ammonia | 50 | ☐ | test | x del |
| CO | Carbon Monoxide | 400 | ☐ | test | x del |
| CO2 | CO:eq | 5000 | ☐ | test | x del |
| Sound | Noise Level | 20000 | ☐ | test | x del |
| Vandal | Move (m0) | 100 | ☐ | test | x del |
| Vape | Large Particulates (10 μm) | 100 | ☐ | test | x del |
| VOC | TVOC | 1000 | ☐ | test | x del |
| Save Changes Above | | | | | |
| Unique id (no prefix) | | 100 | ☐ | + add | |

| Live View | Sensors Events | Actions | Notifications | Device | |
|---|---|---|---|---|---|
| Events | | | | | |
| Event Identifier | Data Source | Threshold | Advanced | Actions | |
| Ammonia | Ammonia | 50 | ☐ | test | x del |
| CO | Carbon Monoxide | 400 | ☐ | test | x del |
| CO2 | CO:eq | 5000 | ☐ | test | x del |
| Sound | Noise Level | 20000 | ☐ | test | x del |
| Vandal | Move (m0) | 100 | ☐ | test | x del |
| Vape | Large Particulates (10 μm) | 100 | ☒ | test | x del |
| smooth4 15 zero4 60 | | | | | |
| VOC | TVOC | 1000 | ☐ | test | x del |
| Save Changes Above | | | | | |
| Unique id (no prefix) | ▼ | 100 | ☐ | + add | |

560 → Email Contents

Subject & Body (Set): %NAME% (%IP%) event %EID% occurred
%EID% value %VAL% exceeded %THR% at %DATE% %TIME%

● On ☐ Off   Reset Delay: 30

Subject & Body (Reset): %NAME% (%IP%) event %EID% stopped
%EID% value %VAL% went below %THR% at %DATE% %TIME%

● On ☐ Off   Set Delay: 30

[Save]

Above, you can use:
%NAME% - device name
%IP% - ip address
%EID% - event id
%THR% - event threshold
%VAL% - sensor value
%DATE% - local date of event
%TIME% - local time of event

Fig. 15

561 → SMTP Settings

Host: [ ]
Port: [25]
Username: [ ]
Password: [ ]
Security: ☐ Normal  ● High (port 465 only)
Sender: [email@email.com]
Recipients: [email@email.com; email2@]

562 → [Save and Test]   ☐ Send Test Email

VMS Settings

Set string: [halo.event.%EID%]   ● On ☐ Off
Reset string: [halo.reset.%EID%]   ● On ☐ Off
Address: [0 0 0 0]
Port: [1234]
Protocol: ● TCP ☐ UDP

[Save]

Above, you can use:
%NAME% - device name
%IP% - ip address
%EID% - event id
%THR% - event threshold
%VAL% - sensor value
%DATE% - local date of event
%TIME% - local time of event

514

HEAT-NOT-BURN ACTIVITY DETECTION DEVICE, SYSTEM AND METHOD

CROSS-REFERENCE TO RELATED APPLICATIONS

The present application is a continuation application of U.S. patent application Ser. No. 17/481,615, filed Sep. 22, 2021, now U.S. Pat. No. 11,302,174, the disclosure of which is incorporated by reference herein in its entirety.

TECHNICAL FIELD

The present disclosure pertains to sensors and, more specifically, to a sensor device, method and system for detecting emissions from heated tobacco products (FUN) or heat-not-burn (HNB) products.

BACKGROUND AND SUMMARY

Individual sensors exist for things like fire, smoke, carbon monoxide, and carbon dioxide. These devices are generally manufactured as single purpose modules that are qualified for life safety applications and designed to fit into traditional low voltage wired burglar alarm system topologies, for example. These units are designed to be very narrow in scope and react only in terms of a single threshold where the monitored gas or condition passes a known life safety threshold. When that threshold is passed, a simple electrical circuit or audible alarm can be triggered.

Buildings inhabited by humans, particularly institutional buildings like schools or commercial environments, or even residential structures, are also faced with environmental conditions where chemicals or particles make it into the air at levels that may not in themselves be toxic to humans, but indicate some sort of activity or occurrence that may either be problematic for a different reason or may be leading up to a situation where actual toxicity might occur.

Such conditions are often caused by human behavior such as, but not limited to, smoking, vaping, sniffing glue solvents, alcohol consumption, and usage of various cleaning products, perhaps in ways unintended by the manufacturer. None of these pollutants have established life safety levels which justify immediate alarms, yet their presence can indicate an overall situation that requires intervention for health, safety, policy or other reason. Further, restrictions on video recording in private areas can reduce the ability to identify a potential perpetrator or determine the cause of a detected event. Even further, video monitoring of premises for visual detection of concerning events is susceptible to failure due to human error or fatigue, obstructed views and other reasons.

The present disclosure pertains, in part, to a sensor device, method and system providing detection of unwanted activities and operable to associate with other systems that can provide additional verification of the actual conditions. Although conventional alarm systems can provide notification, they cannot provide additional verification of quantitative data, or trending display or analysis. Since undesirable activities are often accompanied by sounds that are indicative of human behavior associated with these unwanted activities, embodiments of the sensor device, method and system in accordance with the present disclosure can be operable with an observation system that provides video and audio verification of HTP or HNB activity. In various embodiments, an interface is provided which allows observation systems to present the data and alerts generated by the sensor. Such an interface can be employed to display live and/or recorded levels of detected substances along with live and/or recorded video and/or audio of premises under surveillance.

In various embodiments, the presently disclosed sensor device integrates a multiplicity of environmental sensors as a single monitoring and alerting mechanism, operable to provide a profile of any contaminant in terms of various gases and particles in the atmosphere, quantified in terms of relative concentrations. Embodiments of the sensor device can incorporate a suite of sensor components that can detect oxidizing gases, reducing gases, ammonia, carbon dioxide-equivalent, carbon dioxide, volatile organic compounds, nitrogen dioxide, sound, noise, visible light, humidity, temperature, movement and particulates, for example. In addition to being able to set thresholds and standards for alerting on any of these sensor components individually, embodiments of the present disclosure can develop measurement profiles for specific common substances that can then be differentiated. For example, the measurement profile for heat-not-burn devices might include particles of a certain size and concentration, carbon monoxide, carbon dioxide (and/or carbon dioxide equivalents) and volatile organic compounds, while the measurement profile for traditional smoking might include particles, volatile organic compounds and carbon dioxide. The integrated sensors are packaged according to design embodiments of the present disclosure so as to facilitate channeling of air and/or sound in ways that improve detection accuracy and operation.

It should be recognized that the presently disclosed sensor device can be adapted to include various types of sensors in order to identify and create an event for a multitude of substances. It should be recognized that the sensor device can operate in everyday environments such as homes, schools, commercial buildings, hospitals and hotels, for example. These locations may, for example, require a low-cost solution for identification of various substances, which may be harmful to health, such as secondhand smoke from e-cigarettes or cigarettes, or beneficial such as the verification of disinfectant of a room to decrease the spread of viruses. In various embodiments, a high detection rate of, for example, 95% or better, and a very low false detection rate of, for example, 5% or less can be achieved for HIP and HNB activity. It will be appreciated that the profile makeup for HIP and HNB activity in terms of particles and gas sensors facilitates accurate detection. It will further be appreciated that knowledge of the profile makeup of commonly occurring substances such as hairspray, cooking smoke and body spray, for example, can facilitate proper distinctions to reduce the chance for falsely identifying HIP or BNB activity. In various embodiments, the kinds and number of sensors used is dependent on the substance to be detected, the profile(s) for the substance, and the sensors required to determine it is not a commonly occurring substance which may be misidentified as the substance to be identified, for example.

In various embodiments, the gas sensors comprise metal oxide films micromachined on heated ceramic substrates, although other types including but not limited to ultrasonic, infrared, non-dispersive infra-red, electro-chemical, photoelectric ionization detection and doped or undoped polymer films can be used. The devices can also be provided with two, three or more different detection channels for different gases, for example. Ancillary electronic circuitry can be provided to control power for heating, infra-red illumination generation, visible light generation, ultrasonic sound generation, amplifiers and analog-to-digital converters for signal processing, for example. Ancillary control assists with modifying the behavior of the associated sensors so as to improve their discrimination and/or accuracy.

In various embodiment, the particle detector sensor component uses reflection of laser light to determine particle counts and bin particles into sizes. Other types of particle detectors including but not limited to ultrasonic and ionization can also be used.

In various embodiments, an interface in accordance with the present disclosure can connect to one or more external management systems, such as a video monitoring system, access control system, building management system and/or lighting control system. Spoken key words can be used to trigger events to control egress (lock/unlock doors), control lighting conditions (e.g., safe egress lighted with green LED lights or unsafe ones with red LED lights), or generally create lockdown events.

Video monitoring systems can provide a verification of undesirable activity but are not well adapted for display of the quantitative data produced by the sensor device in accordance with the present disclosure. In various embodiments, the sensor package of the present disclosure includes a facility that generates a visual dashboard embodied in a video stream for revealing the output values, threshold limits, and alert states of one, many or all of the sensor components within the device. This video stream can be displayed within a video monitoring system so as to provide an immediate and in-depth interface to the sensor device.

In various embodiments, detected event communications can be generated by setting one or more thresholds for individual detection channels and by establishing one or more measurement profiles for monitored substances across one or multiple detection channels. When a measurement profile is matched, a detected event communication describing the apparent substance is generated. Embodiments of the sensor device of the present disclosure can include interfaces for video monitoring systems that allow delivery of the generated detected event communications. Embodiments of the sensor device as described herein can also deliver detected event communications through MQ Telemetry Transport (MQTT) publishing or other standard or non-standard interfaces, such as, for example, TCP/IP, HTTP, HTTPS, REST, CANBUS, MODBUS, SNMP and BACNET, effectively interfacing to a wide variety of systems. Any of these communication protocols can be operated over one of many physical network implementations including Ethernet, RS-485, Bluetooth, Wi-Fi, and Cellular data and more.

For a heat-not-burn event detection, embodiments of the present disclosure can establish a profile that is met when particles are measured to exceed a designated threshold while carbon dioxide or CO2 equivalent are measured as not exceeding or being below a threshold. In other embodiments, a profile for a heat-not-burn event detection can be established and met when carbon monoxide exceeds a designated threshold while carbon dioxide or CO2 equivalent does not exceed a threshold. In still other embodiments, a profile for a heat-not-burn event detection can be established and met when particles exceed a designated threshold while total volatile organic compounds (TVOC) does not exceed a threshold. In yet other embodiments, a profile for a heat-not-burn event detection can be established and met when carbon monoxide exceeds a designated threshold while TVOC does not exceed a threshold. In further embodiments, a profile for a heat-not-burn detection can be established and met when both particles and carbon monoxide exceed designated thresholds whereas either carbon dioxide, CO2 equivalent or TVOC does not exceed a threshold. In still further embodiments, a profile for a heat-not-burn detection can be established and met when one of particles or carbon monoxide exceeds a designated threshold whereas carbon dioxide, CO2 equivalent and TVOC do not exceed respective thresholds. It will be appreciated for all of the above examples that exceeding or not exceeding a threshold can be over a period of time or at a set time.

In various embodiments, the sensor device can comprise hardware and firmware elements, including an electronic control system, a case, a shield and a cover. The environmental sensors can be secured as part of the electronic control system and the shield can be formed so as to facilitate proper channeling of air and sound for effective operation.

BRIEF DESCRIPTION OF THE DRAWINGS

FIGS. 8 through 16 are exemplary screen shots in accordance with aspects of the present disclosure.

DETAILED DESCRIPTION

The presently disclosed subject matter now will be described more fully hereinafter with reference to the accompanying drawings, in which some, but not all embodiments of the presently disclosed subject matter are shown. Like numbers refer to like elements throughout. The presently disclosed subject matter may be embodied in many different forms and should not be construed as limited to the embodiments set forth herein rather, these embodiments are provided so that this disclosure will satisfy applicable legal requirements, Indeed, many modifications and other embodiments of the presently disclosed subject matter set forth herein will come to mind to one skilled in the art to which the presently disclosed subject matter pertains having the benefit of the teachings presented in the foregoing descriptions and the associated drawings. Therefore, it is to be understood that the presently disclosed subject matter is not to be limited to the specific embodiments disclosed and that modifications and other embodiments are intended to be included within the scope of the appended claims.

It will be appreciated that reference to "a", "an" or other indefinite article in the present disclosure encompasses one or more than one of the described element. Thus, for example, reference to a processor may encompass one or more processors, a threshold may encompass one or more thresholds, a measurement may encompass one or more measurements, a channel may, encompass one or more channels and so forth.

Figure 1:
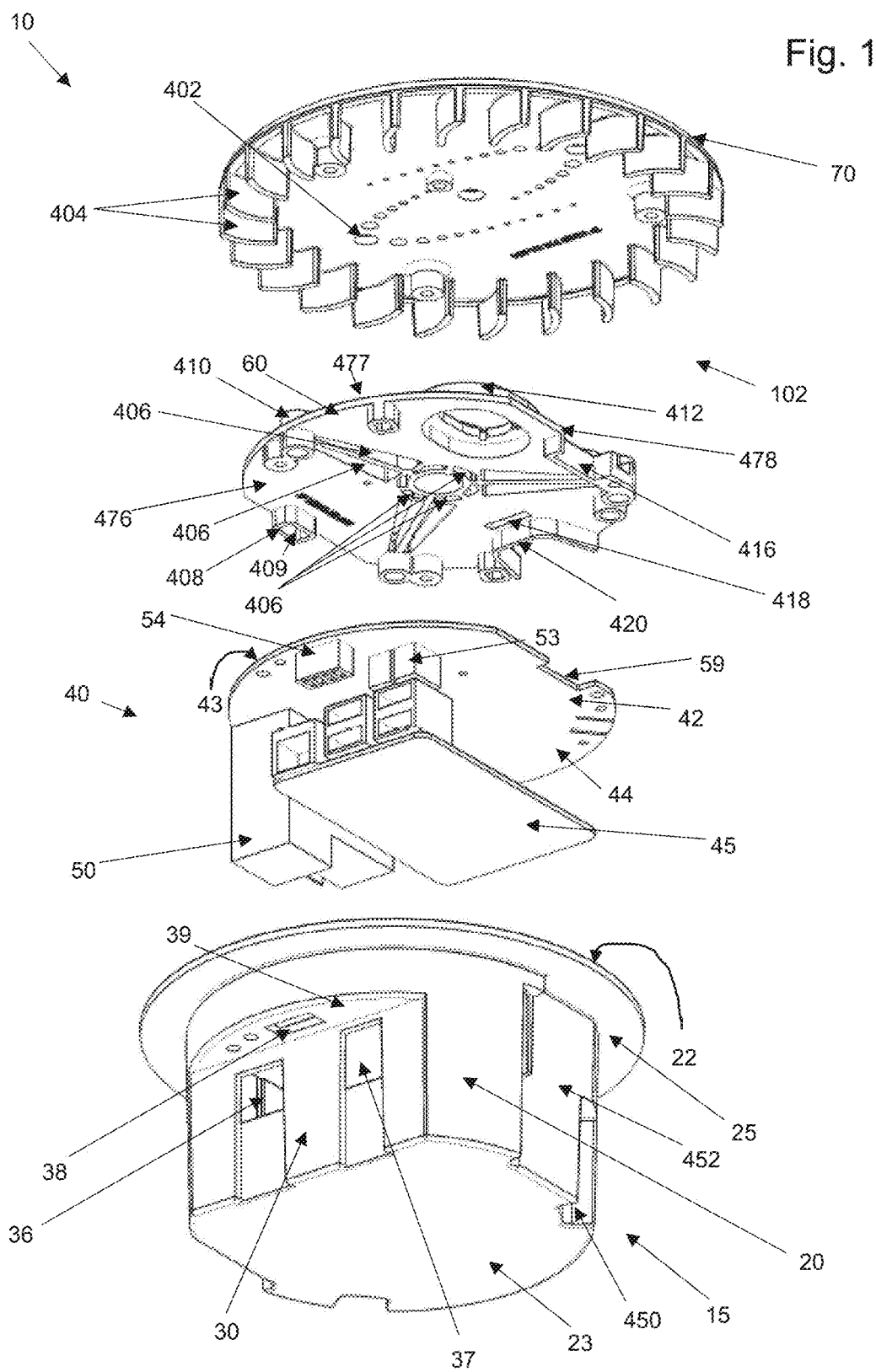
FIG. 1 is an exploded perspective view of the sensor device in accordance with embodiments of the present disclosure.

As shown in FIGS. 1 through 4, in various embodiments, the sensor device 10 can comprise hardware and firmware elements, including an electronic control system 40, a case 15, a shield 60 and a cover 70. The case 15 can be considered a housing for the sensor device, whether alone or in combination with the shield 60 and/or cover 70, The case 15 can be formed of a generally firm but lightweight material such as plastic, for example, with a rim 25, a bottom surface 23 and a substantially cylindrical wall 20 having an open interior 22 for housing the electronic control system 40. The wall 20 can be provided with a face 30 formed with access ports (e.g., network connector 36 and USB 37 ports) to enable connection with various internal components of the electronic control system 40 as described elsewhere herein. In various embodiments, an interface wiring pluggable terminal block (not shown) can be secured to the face 30. As shown in FIG. 1, the face 30 can be substantially planar, and abuts a ledge 39 extending radially inwardly from the wall 20. The ledge 39 can also be formed with one or more access ports (e.g., 38) and is generally parallel to the rim 25.

As further shown in FIG. 1, the electronic control system 40 can include a main computing board 42 having a top 43 and bottom face 44, and a microcontroller or mini-computing device 45 such as a Raspberry Pi™, for example. In various embodiments, a support bracket (not shown) can be secured to the bottom face 44 of the board 42 and is either secured to or otherwise supports the positioning of the microcontroller 45. A particle sensor 50 can be secured to the bottom face 44 and/or the support bracket. A Power over Ethernet (PoE) regulator (not shown), a relay circuit connector 54 and various interface relays 53 can be secured to the bottom face 44 of the main computing board 42. The interface relays 53 link the computing device 45 to the sensor components on the board 42. An analog to digital (A to D) converter is also secured to the main computing board 42. The locations of the elements on the main computing board are established to coordinate with complementary elements on the case 15, shield 60 and/or cover 70, or with one or more complementary channels resulting from placement of other elements on the case 15, shield 60 and/or cover 70.

As shown in FIG. 1, the cover 70 and shield 60 form one or more fluidic channels 102, blocking external physical access to the sensors, Additionally, FIG. 1 shows cover 70 provided with secondary air holes 402 and intake/exhaust fins 404 to facilitate air flow. Air flowing through the air holes 402 and fins 404 effectively flows through one or more fluidic channels formed by the structural elements of the device as shown and described herein. As further shown in FIG. 1, lightening cavities 406 can be provided to reduce the bulk of the shield 60, which may be formed of plastic in accordance with embodiments of the present disclosure. A particle intake wall 408 can also be formed on the bottom surface 476 of the shield 60 and aligned above the particle sensor 50. The particle intake wall 408 forms a particle intake channel 409. A speaker housing 412 is also provided on top surface 477 of the shield 60, along with a boss 410 for secure mating with the outer cover 70. A partial air exhaust 416 can also be formed in the side wall 478 of the shield 60, along with a sensor isolation wall 420. A wiring port 418 can also be formed in the shield 60 to permit the passage of wires, for example.

Figure 2:
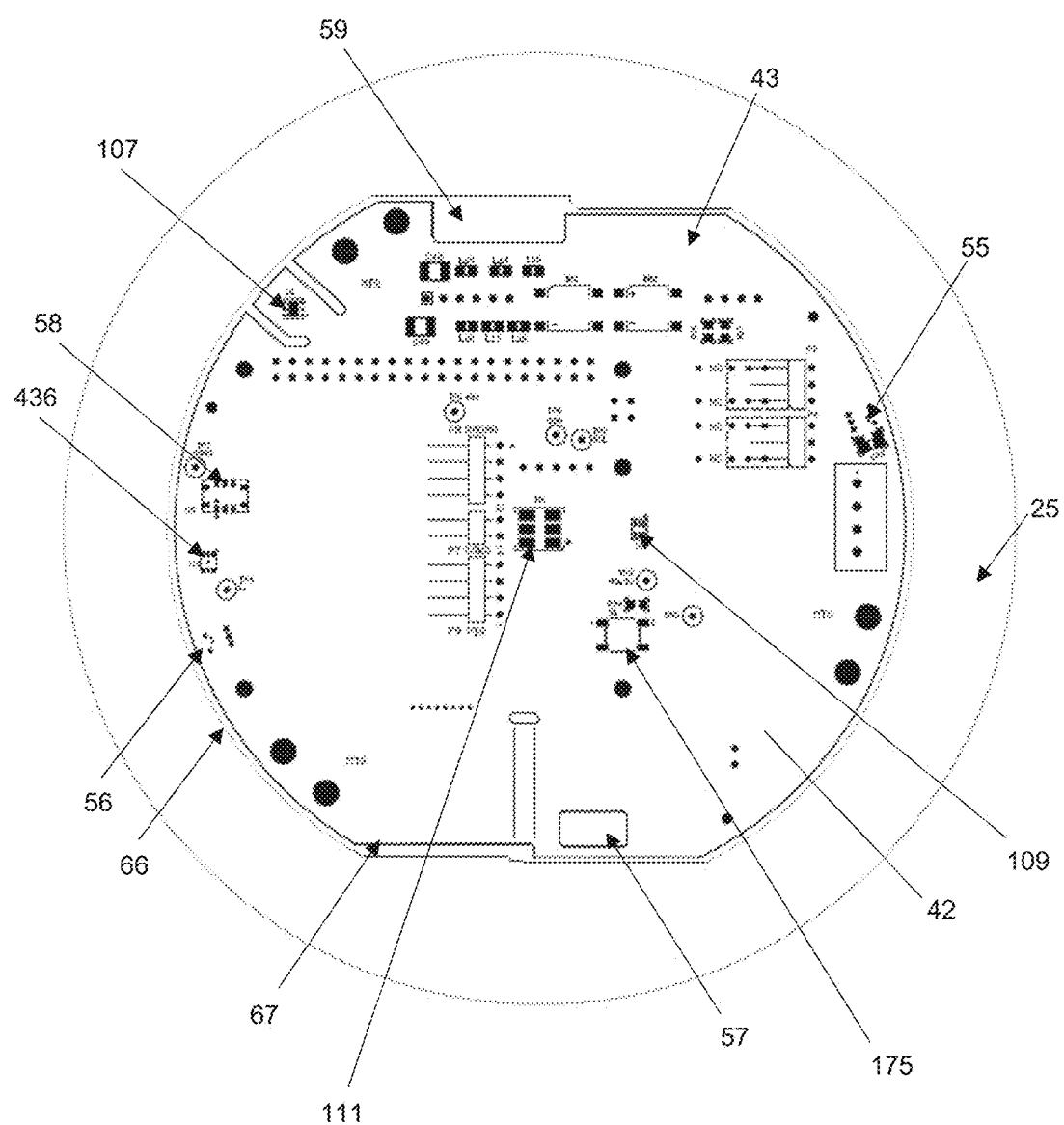
FIG. 2 is a top plan view of the top face of a main computing board positioned within the rim of a case in accordance with embodiments of the present disclosure.

As shown in FIG. 2, a pair of microphones 55, 56 and one or more gas sensors 58 can be secured to the top face 43 of the main computing board 42, along with environmental sensor 107, a sensor 436 for total volatile organic compound (TVOC) and carbon dioxide, an LED display 111 for red, green, blue and mixed color alerting, a light sensor 109, a system reset button 175 and other elements. 12S is an electrical serial bus interface standard used for connecting digital audio devices, and this can be used in connecting microphones 55, 56 to microcontroller 45, for example. In various embodiments, the environmental sensor 107 is a temperature, humidity and barometric pressure sensor which may incorporate 16-bit A to D conversion to for resolution of very small changes in local air pressure. This capability allows for detection of anomalies in air conditioning operation, open windows and open doors, for example. In various embodiments, an accelerometer is employed with or alongside environmental sensor 107. The accelerometer can be secured to the shield 60 or the main computing board 42, or in various embodiments, mounted on an auxiliary PC board plugged into and screwed onto the main computing board 42 under the processor. The accelerometer can determine if the device 10 is being moved or tampered with and can provide an event notification in the event of a detected movement beyond an established threshold.

The accelerometer may also determine if the building or structure itself is moving. Detection and notification of motion and vibration in the structure of a building might provide early warning and additional safety in advance of a dangerous structural collapse. The sensor unit is generally affixed to part of a building's structure such a ceiling. Under these circumstances, the three-axis accelerometer used for tamper detection can also detect motions in the building that are precursors to a structural failure. Thresholds can be set on each axis to provide warnings on excessive motion. Another embodiment could employ processing algorithms, for example a 4-pole bandpass filter, to help discriminate between tamper motion and building motion. Additional discrimination can be provided by incorporation of other means of human presence detection such as a passive infrared sensor to rule out tampering. Another embodiment might use a six or nine axis accelerometer sensor to better discriminate the type or cause of motion. For example, an angular gyro component to the sensor can detect human tampering compared with building motion.

In addition, the main computing board 42 can be formed with air intake 57 and air exit 59 vents to facilitate air flow into and out of the particle sensor 50, respectively. It will be appreciated that embodiments of the particle sensor 50 can be provided with a fan to assist with directing air flow through the vents 57, 59. In various embodiments, the interior 22 of the case 15 is provided with a radially inwardly extending ridge 66 to support the outer edge 67 of the main computing board 42. The board 42 can be secured to the ridge 66 using screws, for example. The board may further be provided with openings for receiving screws or other attachment devices secured to the shield 60 and/or cover 70.

Figure 3:
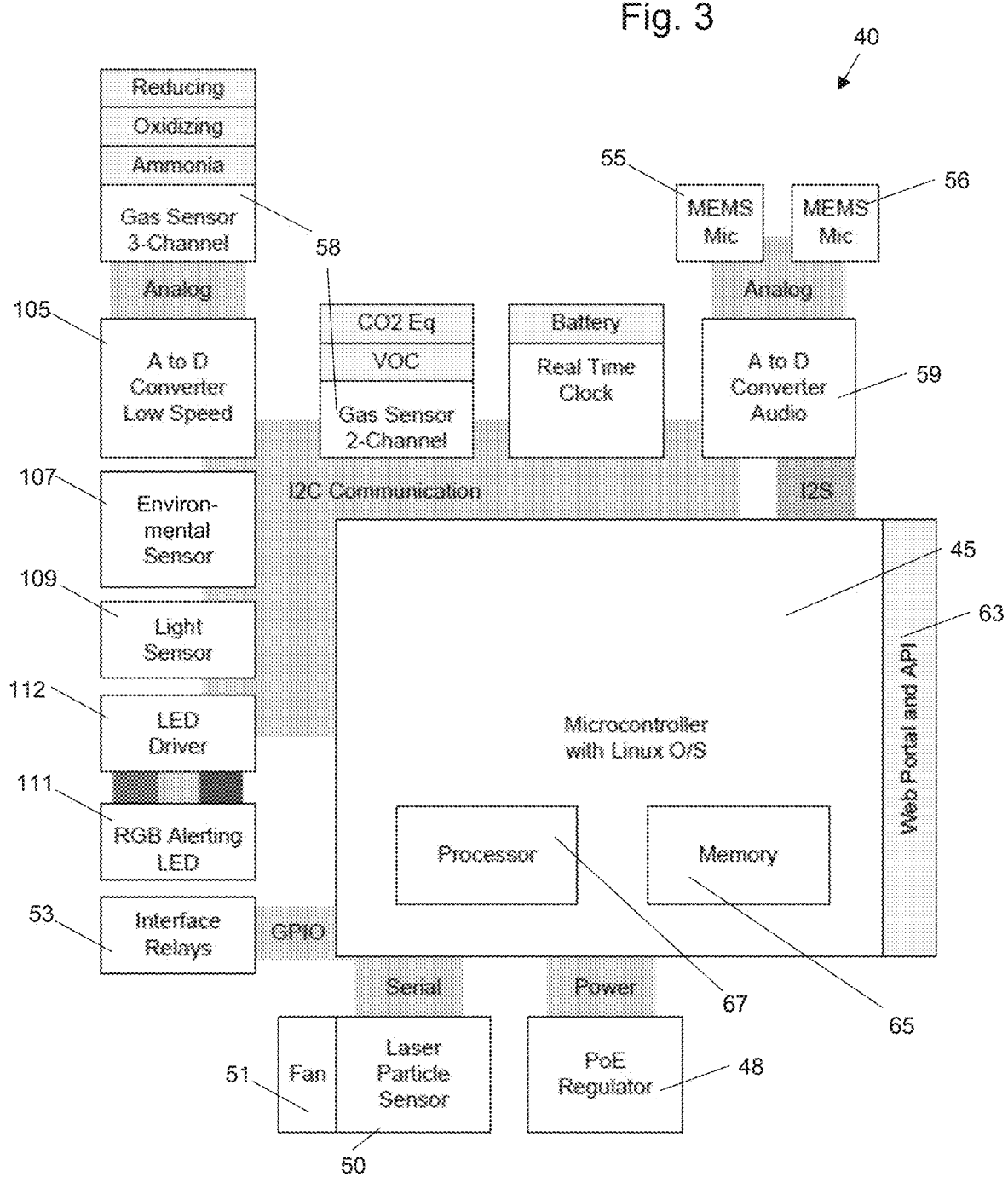
FIG. 3 is an exemplary schematic diagram of an electronic control system in accordance with aspects of the present disclosure.

FIG. 3 shows an exemplary schematic diagram representation of the control system 40. As shown in this embodiment, the control system 40 includes gas sensors 58 including, for example, a three-channel sensor for ammonia, and oxidizing and reducing gases, as well as a two-channel sensor for carbon dioxide equivalent (CO2 eq), and volatile organic compounds (VOCs). In this example, the three-channel sensor output is processed through an analog-to-digital converter 105 and the digital output is communicated to the microcontroller 45 via I2C protocol. I2C is a serial protocol for two-wire interface to connect low-speed devices like microcontrollers, EEPROMs, A/D and D/A converters, I/O interfaces and other similar peripherals in embedded systems. The control system 40 further includes an environmental (e.g., temperature/humidity/barometric pressure) sensor 107 and light sensor 109 in communication with the microcontroller via I2C protocol, for example. The environmental sensor 107 can measure temperature, humidity and/or barometric pressure at the device's location. These measurements can be used to determine comfort of human habitability and can assist general assessment of the operation of any onsite heating, ventilation and air conditioning system. An exemplary sensor is the BME280 sensor. This sensor can provide calibrated, linearized signals in digital, I2C format. Direct interface with a micro-controller is made possible with the module for humidity and temperature digital outputs. Every sensor can be individually calibrated and tested. The resolution of the digital humidity sensor can be changed by command (8/12 bit up to 12/14 bit for RH/T).

In various embodiments, the environmental sensor 107 is connected to the I2C bus of the microcontroller 45 and this is the primary means of transferring data between the controller and the detector. A driver function extracts information from the sensor and makes that information conveniently available to other processes. The driver serves to isolate information consuming processes from any knowledge of the physical or logistical details of the sensor. The driver needs to know the I2C address of the sensor in order to connect to it correctly over the $I^2C$ bus. Since this address is determined by the design of the device and the address configuration set in hardware, it can be embedded in the driver code and need not be a configuration variable. The driver gets information from the sensor by polling it on a regular basis and maintaining the latest temperature, humidity and pressure values in accessible memory buffers. The polling rate is determined by a supplied configuration value. Sensors can also include programmable internal thresholds that generate active triggers when limit values are crossed. These triggers can be communicated to the processor using interrupts, enabling much faster and more deterministic reaction to events than is possible using polling.

The light sensor 109 can be a highly sensitive light sensor with a spectral curve very similar to that of the human eye, for example. Data from the light sensor 109 can be sent to the microcontroller and made available for remote access through the API 63. The light sensor 109 can be useful for determining whether the illumination in the area of operation of the device is suitable for human occupation and whether expected or unexpected illumination is present. For example, if a cigarette lighter is ignited in a bathroom stall, the light sensor 109 may trigger the generation of an alert communication as described elsewhere herein.

In various embodiments as noted elsewhere herein, the environmental sensor 107 includes an air pressure sensor to detect air pressure levels. Such detection can assist in implementations within certain environments (e.g., hospitals and other healthcare facilities) where certain levels of air pressures may be mandated. In various other embodiments, the sensor disclosed herein can be provided with thermal, radar and/or lidar detectors to reliably detect moving or stationary persons or objects. Such sensors can assist with detecting a person moving or even breathing in a room, for example. In various other embodiments, the sensor described herein can be augmented with artificial intelligence, such as voice-activated query and response functionality to enable a user onsite to configure and/or query a device for feedback. In still other embodiments, the sensor device described herein can be provided with various life safety elements and features. Further, ultrasonic detectors sensitive to both fixed object and moving objects in the sensor's environment can be incorporated into embodiments of the present device. In various implementations, each of these above types of sensors may be either single emitter/receiver designs or may be switched array or phased array multiple receiver and/or multiple emitter designs.

In various embodiments, alerting facilities are provided with the sensor device. For example, a red-green-blue (RGB) alerting LED 111 can also be provided as part of the control system 40, having an LED driver 112 in communication with the microcontroller 45 via $I_2C$ protocol. In various embodiments, alerting LED 111 can be exposed on the surface of the device and use full color and intensity control to display various system status and alerting indications. In various embodiments, the LED 111 can be many LEDs in the form of a circle or series of bars to indicate the levels of gas detection via color, number of lit LEDs, or a combination of both. This alerting LED 111 may also be completely disabled for application where "hidden" operation is desirable. Further, the device can include two electrically isolated relays 53 that may be used to connect a standalone unit to a siren/strobe, a conventional alarm panel, or any other low voltage circuit. In various embodiments, two relays 53 are provided, and these may be associated with any two thresholds or rules created in the firmware. It will be appreciated that wired electrical bus connections may include CANBUS, MODBUS, RS-485, and others for wired connections to outside data sources and for direct signaling to external related systems such as HVAC controls, building management and automation systems and others.

The laser particle sensor 50 with fan 51 can communicate with the microcontroller 45 via serial interface, for example, and the PoE regulator 48 is provided for power. The analog signal from microphones 55, 56 is converted using an AD converter 59 which communicates with the microcontroller 45. The microcontroller can further include a memory 65 storing programming for execution by processor 67, and an application programming interface (APT) and web portal 63 to facilitate communications with external systems and programs.

Embodiments of the microcontroller firmware (operating program) can perform several tasks required to implement the intended functions described herein, including file system operations, storage of configuration values, polling all sensors for current data, controlling output devices, web page hosting, API implementation (e.g., MQTT and specific to remote systems), security and login accounts, visual (e.g., JPG, MJPEG, H264 or other video compression technologies) dashboard generation and streaming, processing current sensor data to isolate desired responses, testing responses against thresholds and schedules to develop detected event communications, delivery of detected event communications to external devices, and delivery of current data and detected event communications through API and the visual dashboard as described elsewhere herein.

As described above, the sensor device 10 can include multiple hardware devices, e.g., sensors, that measure physical environmental conditions. These sensors can include a carbon monoxide detection sensor, a carbon dioxide sensor, a particle detection sensor and a volatile organic compound sensor, for example, and can be polled by the central processor 67 to retrieve their current measurements and/or values. The sensor polling operations can include a mixture of direct wired binary logic connections between the controller and peripherals (sensors, LEDs, relays) and serial data communications with specific sensors that are configured for these serial modes. For example, the particle sensor 50 communicates with the controller 45 using the standard asynchronous serial protocol and UART commonly used by RS-232 implementations but at the internal logic levels of 3.3V as appropriate for the controller 45. The output relays are controlled by direct logic level wired connections to the processor 67.

As exemplified elsewhere herein, communication to most of the sensors can be accomplished through a fast, two-wire I2C serial bus for easy connection to a microcontroller or embedded controller. The digital output of the device is inherently more immune to noise when compared to a direct analog interface. In various embodiments, the audio subsystem uses I2C for control and configuration and an I2S bus for transfer of raw audio data. It will be appreciated that appropriate communication protocols are employed with the presently disclosed device and system. For example, the universal asynchronous receiver-transmitter (UART) takes bytes of data and transmits the individual bits in a sequential fashion. At the destination, a second UART re-assembles the bits into complete bytes. Each UART contains a shift register, which is the fundamental method of conversion between serial and parallel forms. Serial transmission of digital information (bits) through a single wire or other medium is less costly than parallel transmission through multiple wires. The UART usually does not directly generate or receive the external signals used between different items of equipment. Separate interface devices can be used to convert the logic level signals of the UART to and from the external signaling levels, which may be standardized voltage levels, current levels, or other signals.

It will be appreciated that communication may be simplex (in one direction only, with no provision for the receiving device to send information back to the transmitting device), full duplex (both devices send and receive at the same time) or half duplex (devices take turns transmitting and receiving).

It will be appreciated that the multiplicity of sensors incorporated into the sensor device 10 interact with the surrounding air in separate ways. For example, accurate temperature measurement requires isolating the temperature sensor from air that has passed through the unit. Further, various sensors must be protected as much as possible from accidental or intentional physical contact. Hardware configuration of embodiments as described herein facilitate meeting these and other requirements for accurate and effective operation.

Figure 19:
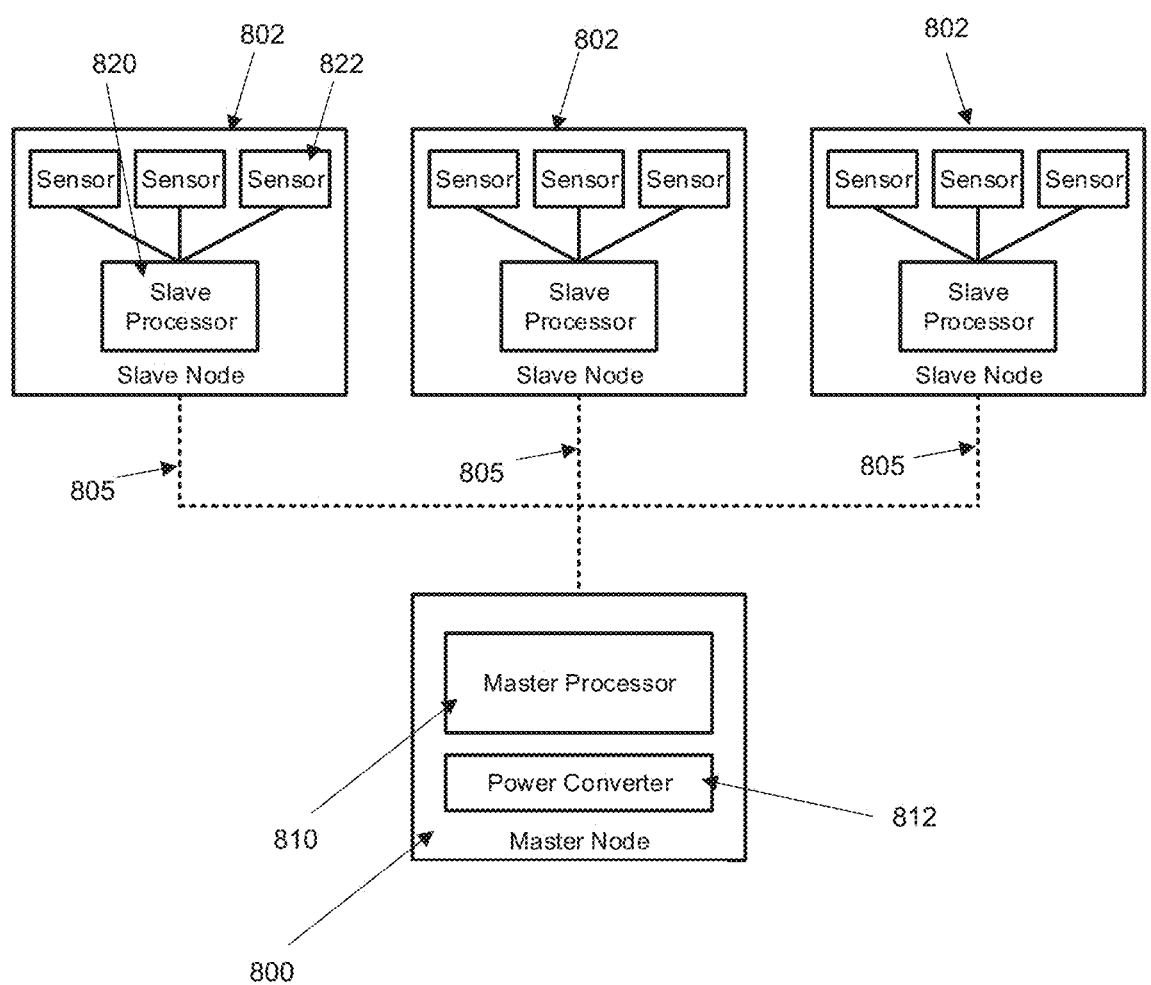
FIG. 19 is a diagram illustrating an embodiment of the system of the present disclosure with a distributed architecture.

In various embodiments, the sensor system is arranged with a distributed topology, such that not all of the sensors and related components are retained in a single device. FIG. 19 illustrates one form of distributed topology, where the connections 805 between the master node 800 and the slave nodes 802 can include data linkage in the form of RS-485 multi-drop serial, CAN Bus, I2C bus, I3C bus, BACNET, 1-wire local control bus, and many other established or ad-hoc transmission protocols and wiring schemes. These connections 805 can also be implemented through wireless protocols such as Bluetooth, Wi-Fi, Z-Wave, LoRa, NFC, and any other standardized or ad-hoc wireless radio) protocol. Further, these connections 805 can be implemented through fiber, infra-red, or ultra-sonic communication protocols.

In various embodiments, these connections 805 can also include power distributed as low voltage AC or DC, PoE standard. Slave Nodes may be battery powered. Batteries can be primary cells, or secondary cells recharged periodically or by solar, wind or other renewable power source. In various embodiments, slave nodes 802 may be powered by energy harvesting.

It will be appreciated that the distributed topology may be two-tiered as shown in the diagram or N-tiered with additional layers of slave nodes designed in intermediate layers. In embodiments that employ a distributed topology, sensors may be spread over a larger physical area without having to duplicate the master processor 810 and power converter 812 multiple times. The distributed topology also allows application of the master processor 810 to a larger number of sensors, allows use of smaller and less conspicuous sensor packages, allows a single master node to present data mapped to physical location within the monitored space, allows a single master node to track movement and propagation of levels and events through a monitored physical space, and allows a single master node to better locate sonic and other event sources in a large physical space. The slave nodes 802 may include a slave processor 820 and one or more sensors 822.

In various embodiments, location accuracy can be enhanced by designing the local connection network to have low and deterministic latency to permit more accurate time comparison than is possible with multiple units operating on a standard Ethernet network, for example. The same local connection network that allows distributed topology can be used to connect interchangeable modular sensor packages to the master processor in the context of a single physical package. The local connection network protocol also permits application of various designs of master processors without redesign of the sensor-based slave nodes.

Figure 4:
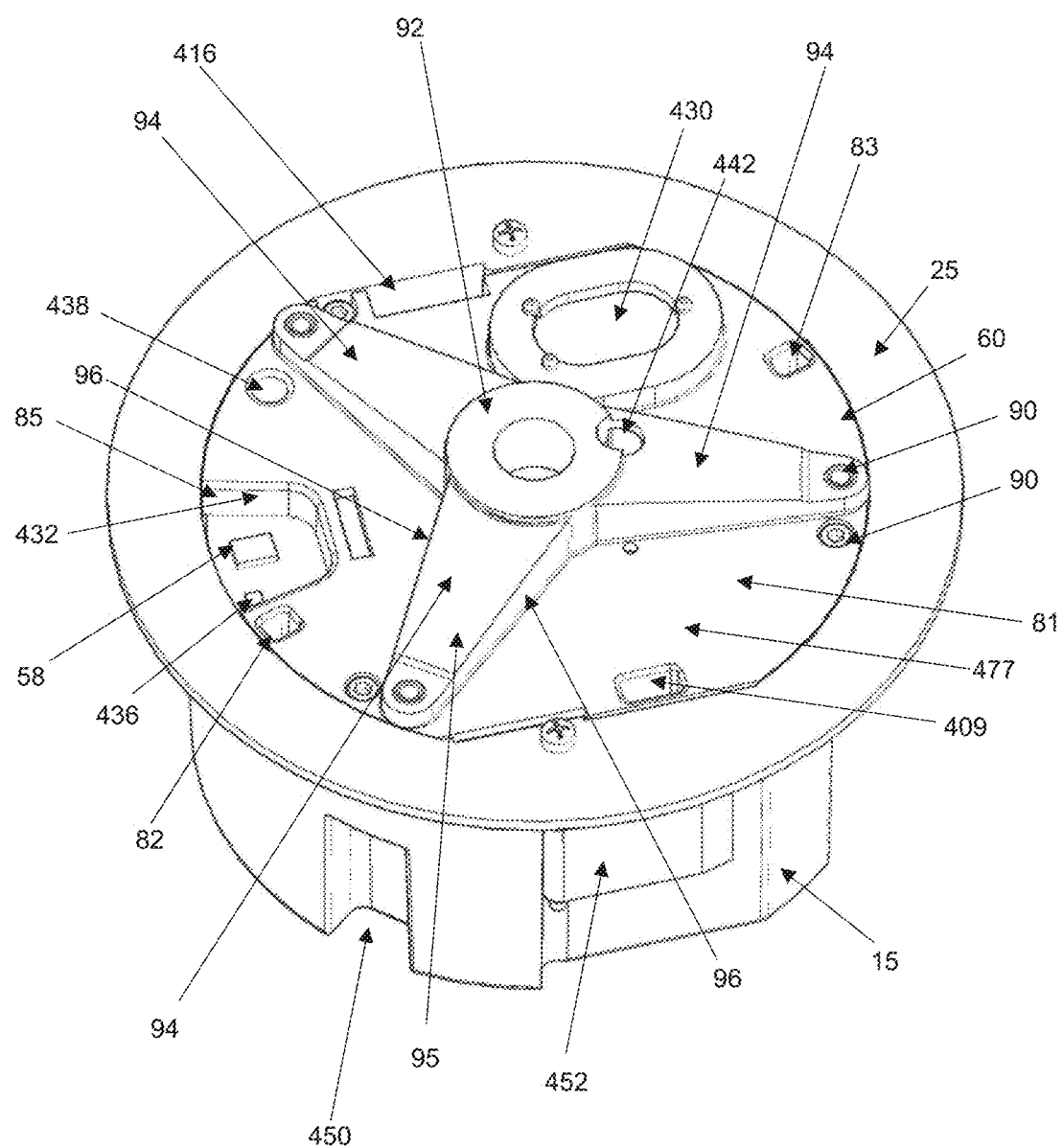
FIG. 4 is a perspective view of a shield member secured to a case member in accordance with embodiments of the present disclosure.

With regard to the embodiments of the disclosure that employ a single integrated device, such as shown in FIG. 4, for example, the shield 60 can be formed with a base 81 having openings formed therein to facilitate operation of the sensor device 10. For example, base 81 can include microphone openings 82, 83 so as not to cover the microphones 55, 56 on the main computing board 42. The openings 82, 83 in shield 60 can also operate as acoustic channels, isolating the microphones from noise from the ingestion fan, for example. In various embodiments, the shield 60 can comprise a single body member of ABS, PVC, or polycarbonate or other suitable material.

Base 81 can also include a gas sensor opening 85 to facilitate exposure of the gas sensor (e.g., three-channel sensor) 58 to the environment in which the sensor device 10 is installed. A particle sensor intake opening 409 and a particle sensor exit opening 416 are provided in the base 81 to align with the intake 57 and exit 59 vents in the main computing board 42. The openings 409, 416 and vents 57, 59 thereby cooperate to form fluidic channels that isolate the intake and exhaust air flows. In various embodiments, at least one of the particle detection sensor and gas detection sensor is adapted with a small heater to provide heated air to pass through the at least one embedded fluidic channel to the environmental sensor. Calculations may be performed based on comparison of the sensor internal temperature with the apparent ambient temperature to provide compensation of heats and provide increase measurement accuracy. In various other embodiments, the embedded fluidic channel is adapted to disperse exhaust air away from intake airflow and directs intake airflow away from the audio component.

Securing device openings 90 can also be formed in the base 81 to facilitate receipt of securing devices such as screws in order to attach the shield to the cover 70, the board 42 and/or the case 15. In various embodiments, an outer support cover 92 is integrally formed with the base 81 and extends above the top surface 477 of the base 81 and the rim 25 of the case 15. The center structure 92 can include one or more support braces/air flow guides 94 which serve to divide and channel the flow of air and sound between the shield 60 and the top face 43 of the main computing board 42 during operation of the sensor device 10. In various embodiments, each support brace 94 can be formed as a top wall 95 formed with a pair of side walls 96, wherein the top wall 95 and side walls 96 form an internal channel on the underside 476 of the shield 60 in which air and sound can travel. It will be appreciated that the center structure 92 further provides a mechanical stiffener for the outer cover 70 when the cover is attached.

Additionally, an isolation harrier wall 432 is shown surrounding the gas sensor opening 85, with the gas sensor 58 and total volatile organic compound (TVOC)/carbon dioxide sensor 436 within the harrier 432. A temperature humidity sensor 438 is also shown, along with an air intake 87 and an air exhaust 88 for the particle sensor 50. A light sensor opening 442 is also shown formed in the shield member 60 in FIG. 12. In various embodiments, the case member 15 can be formed with one or more side recesses 450 to save material and one or more locking clamps 452. A loudspeaker 430 can also be positioned within the speaker housing 412 (shown and described in connection with FIG. 1).

As described above, the sensor device 10 can be provided with one or more gas sensing detectors 58. Many types of gases, aerosols (suspensions) and evaporative products are sensed by gas sensing detector 58 and classified through use of multi-channel gas sensing. Gases are sensed by interaction with specialized metal oxide layers micro-machined onto ceramic substrates which are heated to a specific temperature. These sensors are available as commercial integrated circuits interfaced with the microcontroller (i.e., mini-computing device 45) using analog and protocols. Each sensor provides separate measurements of several general types of gases. These types include, but are not limited to, reducing gases, oxidizing gases, ammonia containing gases, carbon dioxide equivalent, and volatile organic compounds (VOCs), This array of chemistries is sufficient to capture the profile of most commercial products that outgas and most naturally occurring gases including combustion gases.

It will be appreciated that such sensors can suffer the challenge of cross gas response, where a given sensor responds primarily to one type of gas but to a lesser degree to other unintended gases. In various embodiment, programming executable by the processor of the electronic control system 40 functions to resolve these cross responses and provide the best possible indications for specific gases and substances. The physical arrangement of the housing and components so as to facilitate air and/or sound flow according to embodiments of the present disclosure also assist in providing the best possible indications for specific gases and substances.

As described above, the sensor device 10 can also be provided with one or more audio sensors. In various embodiments, audio detection is provided by one or more precision MEMS microphones 55, 56 spaced at the edges of the board 42. To obtain maximum dynamic range and frequency range, the microphones can be pre-amplified and then processed through a separate high-quality audio CODEC connected to the microcontroller 45. Audio can be analyzed via firmware operable via the microcontroller 45 by applying real-time Fast Fourier Transform (FFT) to divide in bands, each band with its own level readout. Additional firmware routines can provide noise reduction, echo cancellation, and directionality, for example.

Figure 5:
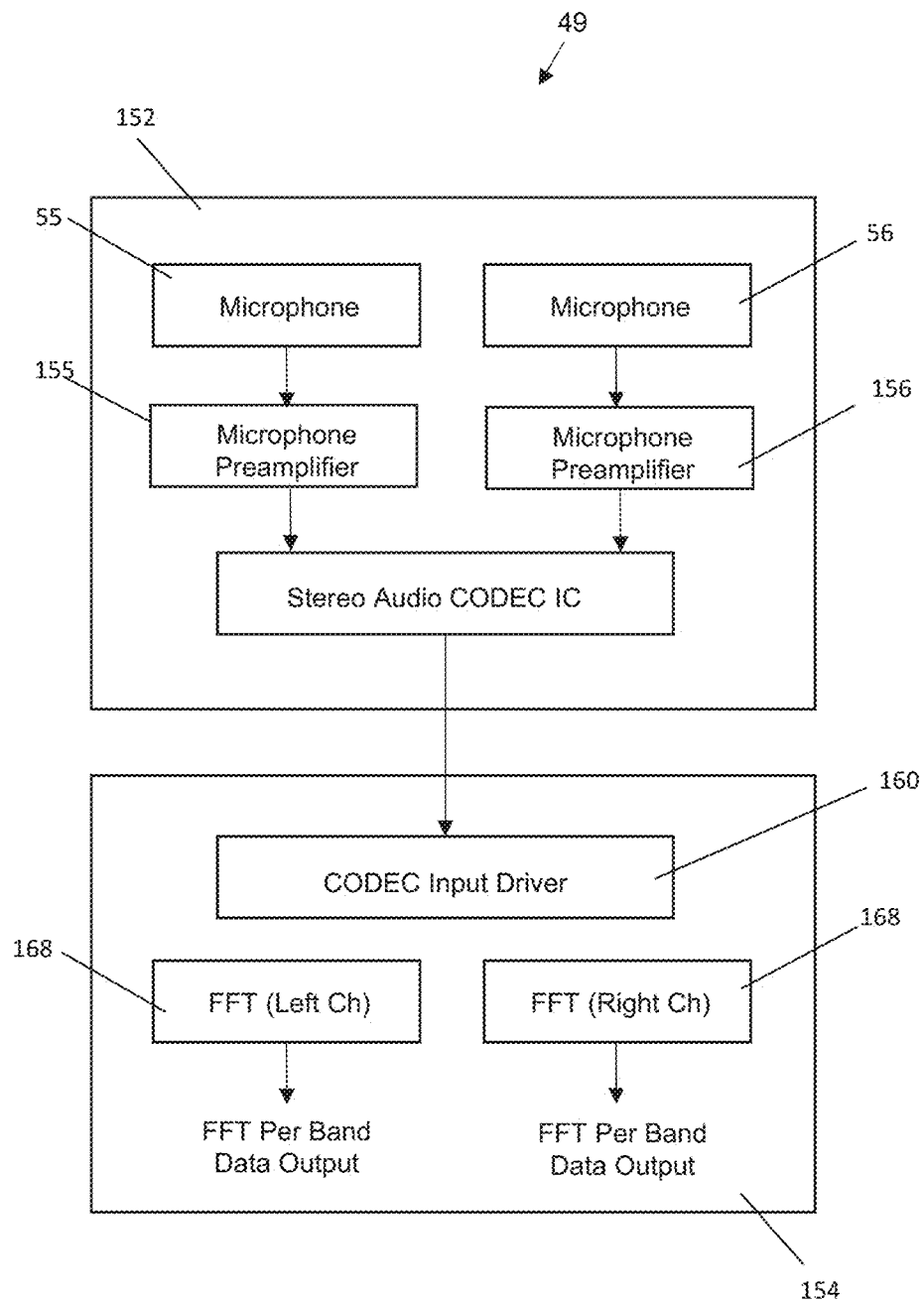
FIG. 5 is an exemplary schematic diagram of an audio system in accordance with aspects of the present disclosure.

FIG. 5 shows a representative audio system design for audio component 49, including the audio firmware 154 and its relationship to the audio hardware 152 in the system. Other designs may be used including an analog or digital filter rather than FFT and larger or smaller audio amplifiers. In terms of audio firmware requirements, a CODEC input driver 160 is provided, which configures the CODEC input hardware element for operation, for example, at 44 Kbps sampling rate and 16-bit dynamic range and stereo (2-channel) operation. This configuration choice can optionally be derived from the overall system configuration file that can be uploaded from a remote network source, for example. The digitized audio input from each microphone can be pre-amplified by preamplifiers 155, 156 and processed through a firmware FFT analysis routine to develop a set of outputs with numeric values that correspond to the audio levels of each of the bands defined for the FFT 168. The two (2) arrays of these frequency/value pairs can be made available to subsequent anomaly detection processes. In various embodiments, the configuration of the Left and Right FFT channels is determined by parameters for number of bands, band frequency centers, processing bit depts., and processing rate. These parameters can be derived from the overall configuration file uploaded to the system. Numerical levels and the first derivative of these levels can be further processed to determine the most likely external conditions being experienced by the sensor device.

Figure 20:
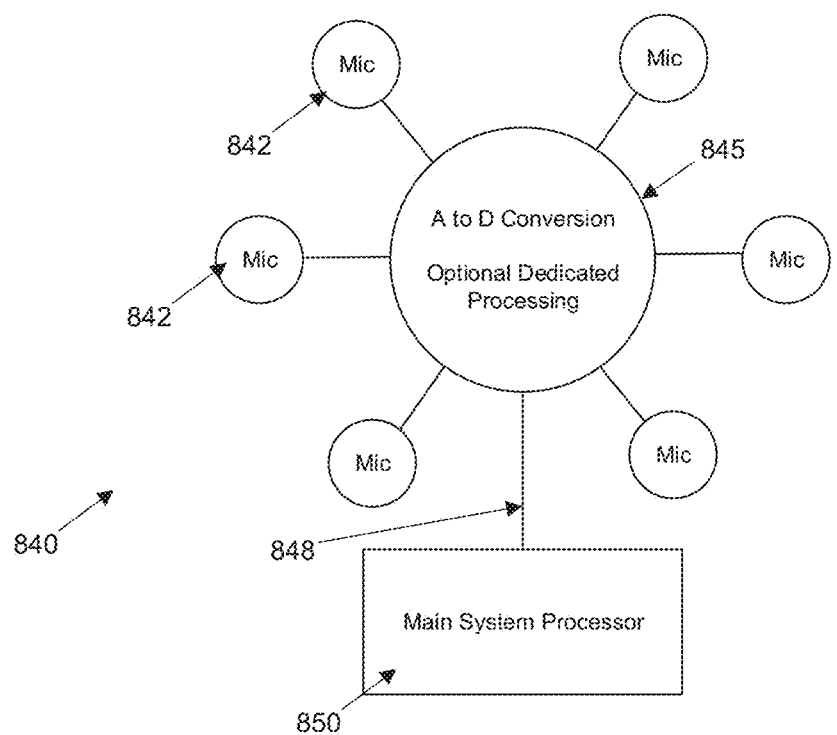
FIG. 20 is a diagram showing an acoustic microphone array in accordance with embodiments of the present disclosure.
Figure 21:
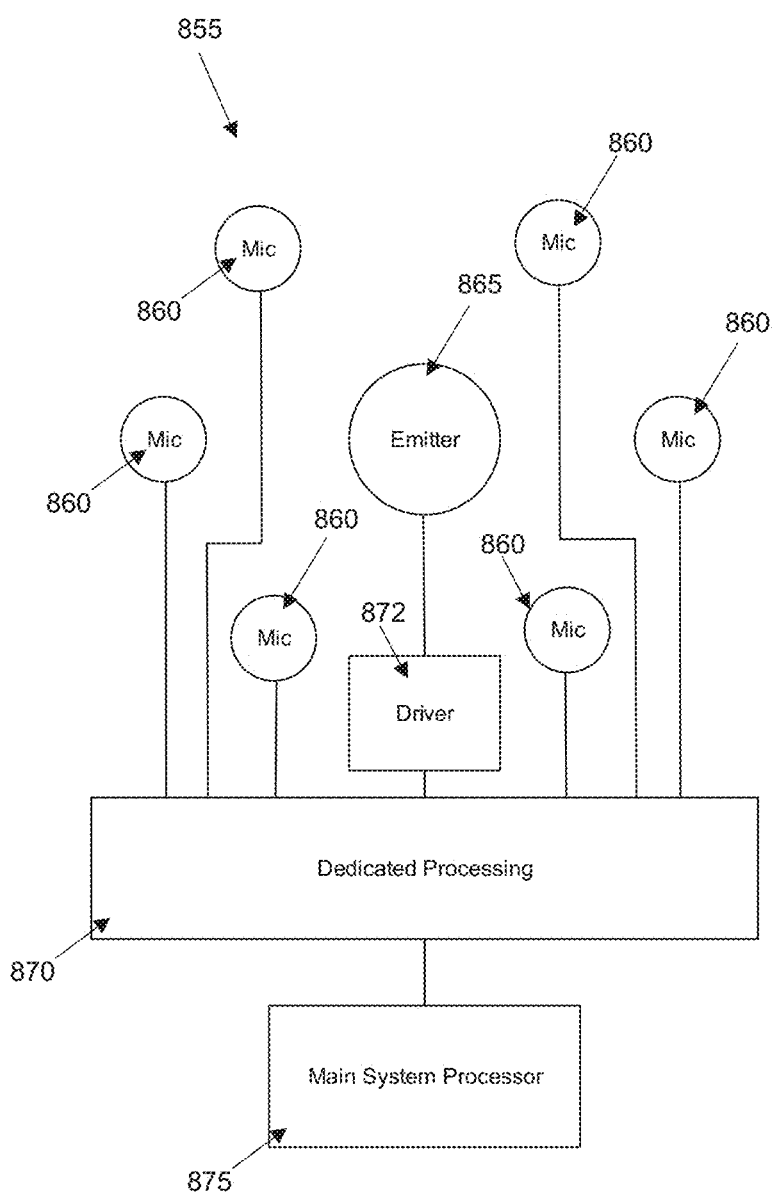
FIG. 21 is a diagram showing phased array ultrasonic object detection in accordance with embodiments of the present disclosure.

In various embodiments, a larger number of microphones and A to D converters is employed to implement noise suppression, echo cancellation, beamforming and other techniques that improve the specifics of sound discrimination. As shown in FIGS. 20 and 21, the presently disclosed system can incorporate a method of combining an acoustic microphone array with an acoustic phased array echo sensor to create a more space efficient, cost efficient, and minimalized hardware system that implements both capabilities.

FIG. 20 depicts an acoustic microphone array 840 together with required analog to digital conversion and optional dedicated processing 845 and a connection 848 to the main system processor 850. Such a configuration can be implemented with MEMS microphones (e.g., 842) and dedicated processing in the form of either DSP or a gate array but may be implemented in other ways. Arranging a microphone array 840 together with optional dedicated processing 845 provides for beam forming, noise rejection, and echo cancellation to improve the operation of algorithms that analyze sound for the purposes of key word recognition, speech recognition, glass break detection, aggression detection and other specialized operations as disclosed herein. For example, in various embodiments, the system may detect a substance and trigger a detected event communication. The system or an operator, upon receiving the detected event communication, may respond with a query via the loudspeaker to any person who may be present in the area. For example, if the detected substance is smoke, the query may ask the person to confirm whether there is a fire at the location or some other cause of smoke.

In various embodiments, such as shown in FIG. 19, the array of microphones is physically arranged at specific distances and in a specific geometry. Dedicated processing is often used to perform the large number of calculations in real time as required for such a configuration. In various embodiments, such as shown in FIG. 21, an array 855 of acoustic sensors 860 together with one or more acoustic emitters 865 can be used to implement the detection of physical objects (e.g., mechanical, humans or animals) within a region and motion of these objects. Such a system can operate at ultrasonic frequencies outside the normal range of human hearing to avoid annoyance of humans in the area. The sensing capability is implemented by short pulses of ultrasound emanating from the emitter 865 being reflected from objects in the area of interest and being thereby returned to the microphones 860. Each microphone 860 is at a different distance from the reflecting object and the pulses of sound return at different times and/or with different phase relationships. Additionally, the frequency of the return may be shifted by doppler effect if the reflecting object is in motion. Dedicated processing 870 can be employed to control, via a device driver 872, the emission of the pulses as well as the measurement of time and optionally phase of the echoes in order to calculate the absolute positions of objects in the area of interest. Such an acoustic echo detection system might commonly operate in the ultrasonic frequency range between 25 KHZ and 50 KHZ most commonly at 40 KHZ, for example. The dedicated processor 872 is in communication with main processor 875, as shown in FIG. 21.

In various embodiments, the presently disclosed system can be implemented by combining the previously described audible listening microphone array of FIG. 20 with the phased array ultrasonic object detection system of FIG. 21. The MEMS microphones employed in the audible frequency range listening system have very effective responses in the ultrasonic range from 28 to 40K HZ. It will be appreciated that the physical arrangement of microphones required and the connections to A to D converters can be the same for both types of systems. The sampling rates of the A to D converters must be increased from the typical 44,000 samples per second to 96,000 samples per second or more to allow operation with the ultrasonic frequencies. As long as the audio levels are maintained in the linear region of the microphones, the ultrasonic emissions do not interfere with the audible frequency reception. The same DSP (digital signal processor) can perform the audible frequency beam forming, echo cancellation, noise filtering and audible detection functions, and simultaneously, the time and phase measurements required for object detection. The net result is the implementation of both the dedicated audible signal detection system and the ultrasonic object and motion detection system with a single set of hardware in a single physical space.

As further described elsewhere herein, the sensor device 10 can also be provided with one or more particle sensors 50, such as a universal particle concentration sensor, which can be used to determine the number of suspended particles in the air, i.e. the concentration of particles, and output them in the form of a digital interface, as described elsewhere herein. This sensor measures the concentration of suspended particles in the air to provide correct concentration data over time. It will be appreciated that the scattering principle can be used in this sensor, i.e., it produces scattering by utilizing structured light to irradiate suspending particles in the air, then collects scattering light at a specific angle, and finally obtain the curve of scattering light changes over time. Equivalent particle diameter and the number of particles with different diameter per unit volume can be calculated by the microprocessor by using, for example, MIE theory.

Figure 6:
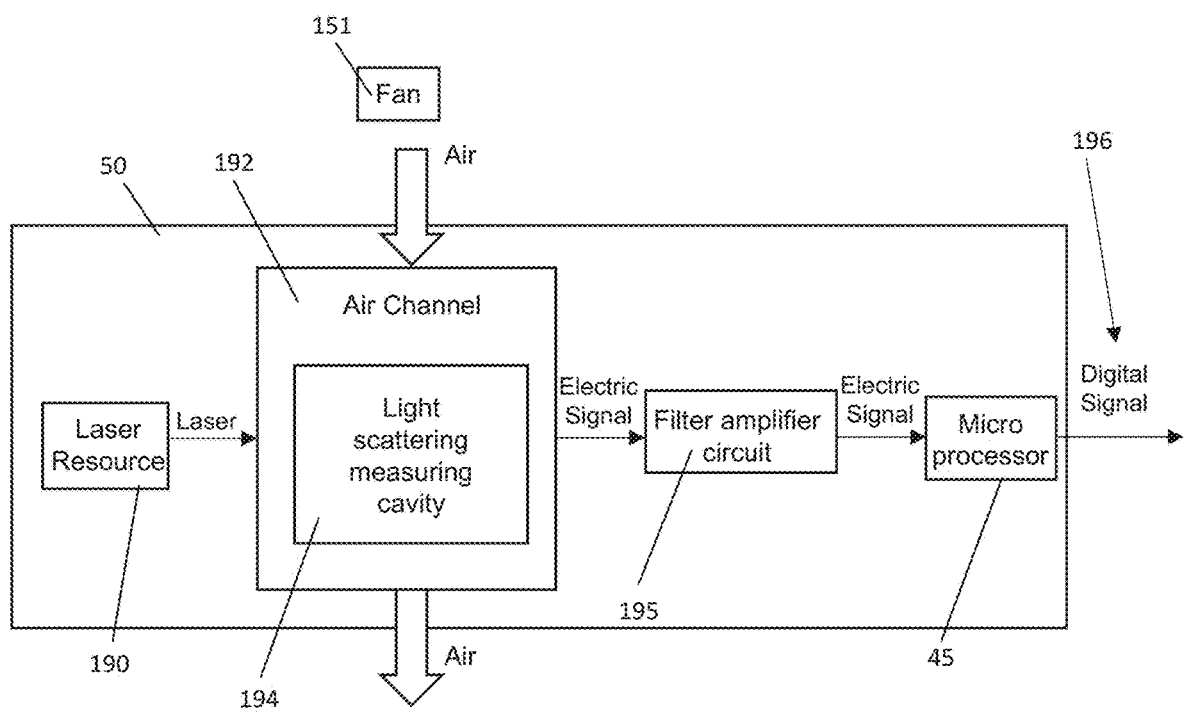
FIG. 6 is an exemplary schematic diagram of a particle sensor in accordance with aspects of the present disclosure.

In various embodiments, the particle detection sensor 50 can be a laser reflection particle detection sensor, and can include an ingestion fan 51, wherein the ingestion fan is secured within the housing so as to induce air flow across the particle detection sensor 50 in a way that facilitates accurate and effective readings. The particle detection sensor can detect the presence of smoke and vaping, for example. A schematic diagram illustrating an embodiment of the particle sensor 50 is shown in FIG. 6. As shown therein, the particle sensor 50 includes a laser resource 190 which can emit a laser to illuminate particles directed by the fan 51 across an air channel 192 and light scattering measuring cavity 194. The resulting electric signal is processed through a filter amplifier circuit 195 and microprocessor 45, and a digital signal output 196 is produced. In various embodiments, the output of the particle detection sensor 50 is provided as the quality and number of each particles in size bins with each of three different sizes per unit volume, where the unit volume of particle number is 0.1 L and the unit of mass concentration is .mu.g/m.sup.3. The output results can be binned into four or more categories: 0.1 to 0.3 uM, 0.3 to 1.0 uM, 1.0 to 2.5 uM, and 2.5 to 10 uM. Based upon the types of particulates to be detected, a particle detection sensor 50 with the ability to detect only one particulate size can be used. For example, 2.5 uM particles are characterized as more dangerous to humans then 10 uM particles at the same density. Thus, in various embodiments, a sensor may be set to detect particulates of size 2.5 uM. In embodiments with six, eight or other numbers of bins, the measured particles can range in size from 0.1 uM to 10 uM, for example.

It will be appreciated that the light and/or illumination sensor 109 can be provided with a very large dynamic range, pseudo human eye response, and other features that make it useful in connection with the present disclosure. In one or more embodiments, a light-to-digital device is employed as the light sensor. Such a device can include on-chip photodiodes, integrating amplifiers, ADCs, accumulators, clocks, buffers, comparators, a state machine, and an I2C interface. Such a device can also combine one photodiode (CHO), which is responsive to both visible and infrared light, and one photodiode (CHI), which is responsive primarily to infrared light. Two integrating ADCs simultaneously convert the amplified photodiode currents into a digital value providing up to sixteen bits of resolution. Upon completion of the conversion cycle, the conversion result is transferred to the data registers. This digital output can be read by a microprocessor through which the illuminance (ambient light level) in lux is derived using an empirical formula to approximate the human eye response.

In various embodiments, the light sensor 109 provides a separate pin for level-style interrupts. When interrupts are enabled, and a pre-set value is exceeded, the interrupt pin is asserted and remains asserted until cleared by the controlling firmware. The interrupt feature simplifies and improves system efficiency by eliminating the need to poll a sensor for a light intensity value. An interrupt is generated when the value of an ADC conversion exceeds either an upper or lower threshold. In addition, a programmable interrupt persistence feature allows the user to determine how many consecutive exceeded thresholds are necessary to trigger an interrupt. Interrupt thresholds and persistence settings can be configured independently.

Similar to other sensors in FIG. 3, the light sensor 109 can be connected to the I2C bus of the microprocessor and this is the primary means of transferring data between the controller and the detector 109. A firmware driver function is included that extracts information from the sensor and makes that information conveniently available to other processes. The driver serves to isolate information consuming processes from any knowledge of the physical or logistical details of the sensor. The driver needs to know the I2C address of the sensor to connect to it correctly over the I2C bus. Since this address is determined by the design of the device and the address configuration set in hardware, it can be embedded in the driver code and need not be a configuration variable. The driver gets information from the sensor by polling it on a regular basis and maintaining the latest values in accessible memory buffers. The polling rate is determined by a supplied configuration value. Depending on the system design, the driver may also include high and low thresholds that are set as either fixed values or percentages of rolling average values maintained by the driver. These thresholds are evaluated after each polling actions and set flags or trigger other processes when crossed. The threshold values and rolling average durations are provide by configuration values. An optional part of the design is the use of a hardware interrupt optionally provided by the light sensor device. This interrupt is triggered whenever the light level is above a user-set upper threshold or below a user-set lower threshold. In various embodiments, the threshold detection mechanisms as described herein may include timers and combinational computations to improve selectivity and reduce spurious alarms. The configuration of filters and timers and combinational computation may be set by users (e.g., 78 in FIG. 7) through drop-down menus and a simple embedded scripting language, for example.

The sensor device 10 can be provided as part of an integrated system including a video monitoring system (e.g., 122 in FIG. 7) comprising one or more video cameras adapted to record video of a surveilled premises. The video camera(s) can transmit recorded video and optionally audio to a system such as external management system 124 in accordance with communication methods as will be understood to those of ordinary skill. The sensor device 10 can receive monitoring data from one or more of the group of sensors, which can include the particle detection sensor 50, gas detection sensor(s) 58, light detection sensor 109, environmental sensor 111 and audio component 49, and can also generate a profile of one or more detected substances, wherein the profile specifies relative concentrations of gases and particles, such as in numeric form, for example.

In embodiments of the present disclosure, different profiles can be established and stored in order to represent factors that, if determined to be present upon evaluating readings from one or more sensors, facilitate determinations, communications, alerts, detected event notifications and other actions as disclosed herein. For example, a profile can be considered as one or more specific measurements or ranges of measurements of one or more of a group of sensors at a specific time and/or over a period of time. For example, a first profile may identify one event as the exceeding of a baseline or threshold measurement for an element as taken by a given sensor. A second profile may identify another event as the exceeding of a baseline or threshold measurement for a first element as taken by a first sensor coinciding with the exceeding of a baseline or threshold measurement for a second element as taken by a second sensor. A third profile may identify yet another event as the exceeding of a baseline or threshold measurement for a first element as taken by a first sensor coinciding with a baseline or threshold measurement not being met or exceeded for a second element as taken by a second sensor.

Profiles can be established based upon the ability to identify one or more specific events with a high degree of probability. Further, profiles can be established for one or more of a group of sensors in an effort to prove a negative, i.e., that one or more measurements provides a high degree of probability that a profiled event has not occurred. It will be appreciated that, for a given profile, one or more of a set of sensors may be required to exceed a set threshold while another one or more of a group of sensors is expected to not exceed (i.e., be measured at or below) a defined threshold as described above. A profile can define the expected characteristics of an event for which a detected event notification or other action is required.

For instance, when the detected substance is gases and/or particles from e-cigarette (i.e., vaping) activity, the "vape" profile may provide details that exclude carbon dioxide and volatile organic compounds, which may include such elements and related sensor measurements being ignored or may include such elements and related sensor measurements being at or below a designated threshold for each such element. For purposes of the present disclosure, the term "nape" may be employed to denote the activity of inhaling and exhaling the aerosol or "vapor" produced by an e-cigarette or similar device, and "nape" may further be employed to denote the actual gases, aerosols and/or particles from the vaping activity. When the detected substance is smoke, the smoke profile may provide details of particles, volatile organic compounds and carbon monoxide. When the sensor device determines that at least a portion of the received monitoring data is indicative of an exceeded threshold and/or when the received monitoring data matches that of a generated profile, a communication such as a detected event communication can be transmitted to a user or communications device. In various embodiments, the detected event communication is transmitted to the video monitoring system to initiate video recording of the premises.

Figure 7:
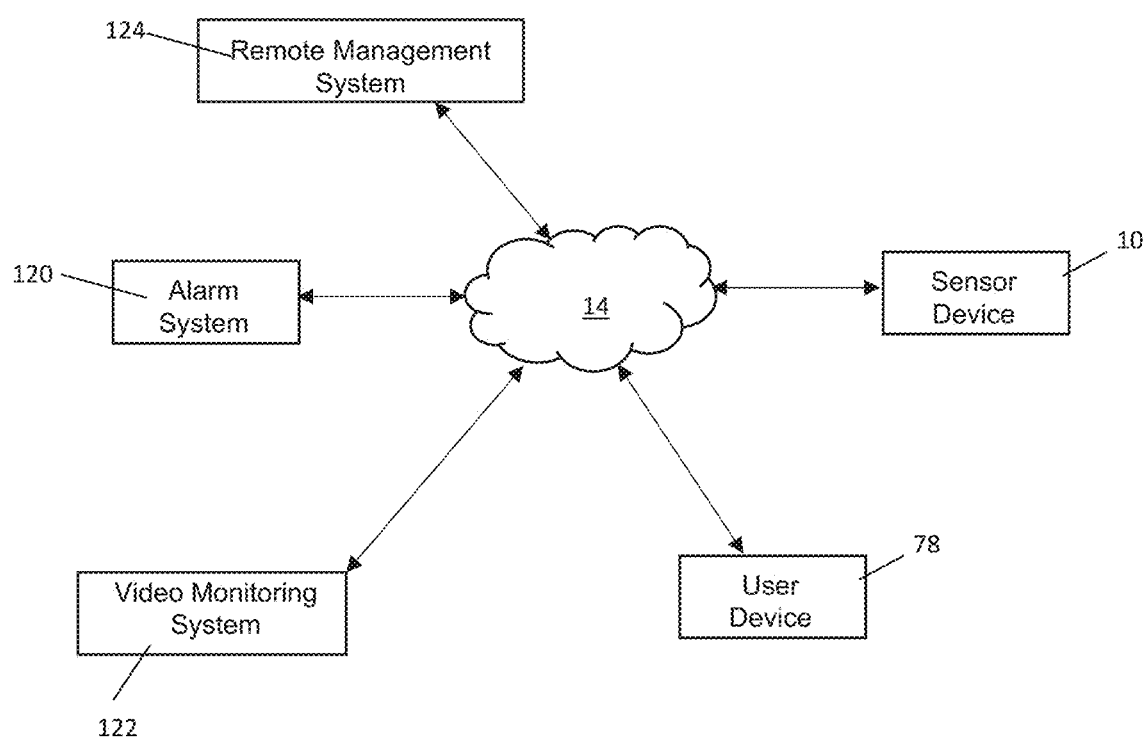
FIG. 7 is an exemplary architectural diagram in accordance with embodiments of the present disclosure.

As shown in FIG. 7, the sensor device 10 is operable to connect to a network 14 to provide real-time analysis, inform other systems such as an alarm system 120, video monitoring system 122 and remote management system 124, and provide other functions as described herein. A communications device 78 such as a desktop computer, laptop, notebook, mobile device, personal communications device such as a smartphone or other computing device can communicate via network 14 to various systems, including with remote system 124 to configure and/or monitor the sensor device 10. In various embodiments, the microcontroller 45 runs an operating system such as Debian Linux, Windows, Android, iOS or other operating system together with dedicated applications. The device 45 is provided with sufficient physical input/output (I/O), a memory and processing power for real-time analysis and the other functions, wherein the functions are executed by a processor executing programming instructions stored in the memory. As described elsewhere herein, in various embodiments, the sensor device 10 includes a PoE; power interface and regulator delivering 5 VDC for system operation. This can be farther sub-regulated to 3.3 VDC and 1.8 VDC for certain components.

In various embodiments, programming stored in memory causes the processor to receive monitoring data from one or more of the group of sensors including the particle detection sensor 50, gas detection sensor 58, light detection sensor 109, environmental sensor 107 and audio component 49, determine that at least a portion of the received monitoring data is indicative of an exceeded threshold and transmit a detected event communication. The received monitoring data measures and reflects the responses of one or more of the group of sensors to one or more specific substances to reduce the effect of cross coupling and cross measurement between the sensors. The received monitoring data from the particle detection sensor can be merged with t received monitoring data from the gas detection sensor to more accurately detect specific substances.

Figure 8:
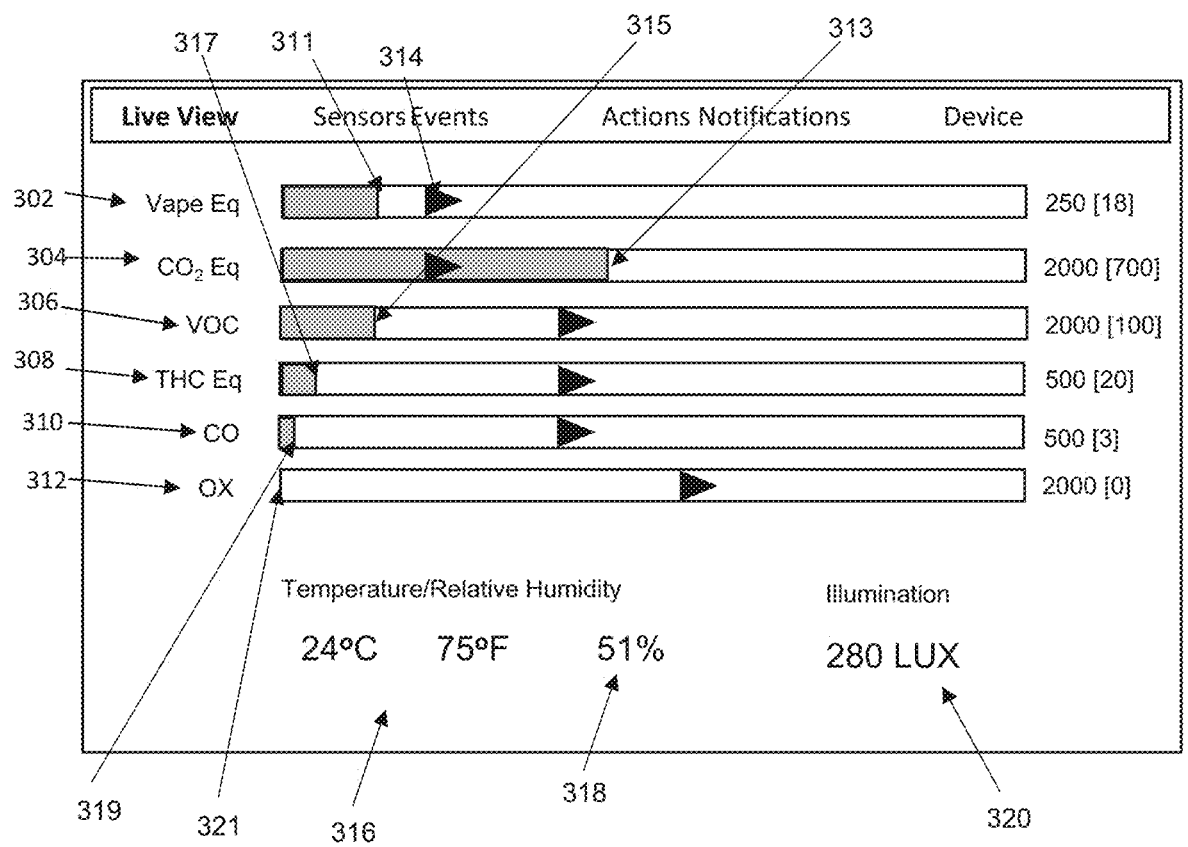

In various embodiments, a web-based user interface (e.g., associated with device 78) provides various functionality, including allowing a user to configure basic settings using typical 1.5 web browser software. FIG. 8 illustrates an example live view status page 300 that provides information on the sensor output, largely in graphical form. As shown in FIG. 8, the level 311 of vape 302, the level 313 of carbon dioxide equivalent 304, the level 315 of VOC 306, the level 317 of THC equivalent 308, the level 319 of carbon monoxide 310 and the level 321 of oxygen 312 are shown, along with threshold levels (e.g., 314) for each gas as set during configuration. In various embodiments, the sensor device can differentiate between vape detected both with and without THC, heat-not-burned-devices, as well as traditional cigarettes. Temperature 316, relative humidity 318 and illumination level 320 can also be shown. It will be appreciated that alternative displays are envisioned and supported herein.

In addition to a status page, a "configuration page" can be provided (not shown) and used to set up one or more devices, and that include, for example: server IP address; server port; server user ID; server password; user DHCP; local IP address; local port; local user ID; local password; allow remote firmware upgrade [T/F]; enable local security [T/F]; defaults will be designed to allow local connection for initial configuration. In addition to a status page, an "about page" can be provided for, for example, company information, hardware model information, and firmware version.

With regard to the API 63, functionality in accordance with embodiments of the present device and system can be primarily configured, controlled and accessed through the Web Services REST API. The functionality of the API can be divided into three (3) sections: Configuration; Status; and Alerts. The configuration information can be contained, for example, in a single JSON, XML or non-standard format file that includes all required settings and values for the operation of all functions except those values involved with addressing and contacting a remote server, such as a server associated with remote system 124 in FIG. 7, for example. The API includes functions that allow transferring this file to and from a remote server (e.g., 124) as commanded from the server side. The internal operation includes buffering (storing) this file in the device during an inbound transfer and performing an integrity check before replacing the "old" settings. The "old" settings are also stored so that the device can return to the previous (working) settings if it fails to work with the new settings. This return can be commanded through the API or by a local physically controlled process.

In one or more implementations, the API enables a server to request current status values from one or more of the sensors. The design has variable granularity so that a single web services request can contain a list of one or many sensors with the result returned as a snippet of XML, or JSON. In general, the server can poll the devices for status data, with the more critical data being polled more frequently. The status API provides comprehensive data suitable for examination and logging but is not intended for alarm/detected event actions.

Further, alerts (i.e., detected event communications) can comprise data delivered to the server in a timely manner. Such data can be the result of the output of rules or processes within the device that generally involve a value or sensed behavior crossing a preset threshold, as shown and described in connection with FIG. 8. Alerts can be transmitted as small snippets of XML or JSON, which are pushed by the device to an accessible web service on the server. Alert transmissions can be provided for timely warning and alarm messages which are expected only infrequently. In one or more implementations; such transmissions are not under control of the remote server and use of this mechanism for general status messages can result in overloading the central server due to random bunching as well as delivery of substantial unnecessary data. ONVIF can be employed, which is an open industry forum for the development of a global standard for the interface of IP-based physical security products. In various embodiments, the ONVIF profile C can be employed as an alternate interface for detected event transmissions, enabling direct interoperability with any third-party video management system (VMS) or physical security management system (PSIM) that supports the profile for detected event messages, without the need for a special integration programming or connectors. Configuration data can include a section for storing connection and authentication values for this external ONVIF system, in various embodiments.

Figure 9:
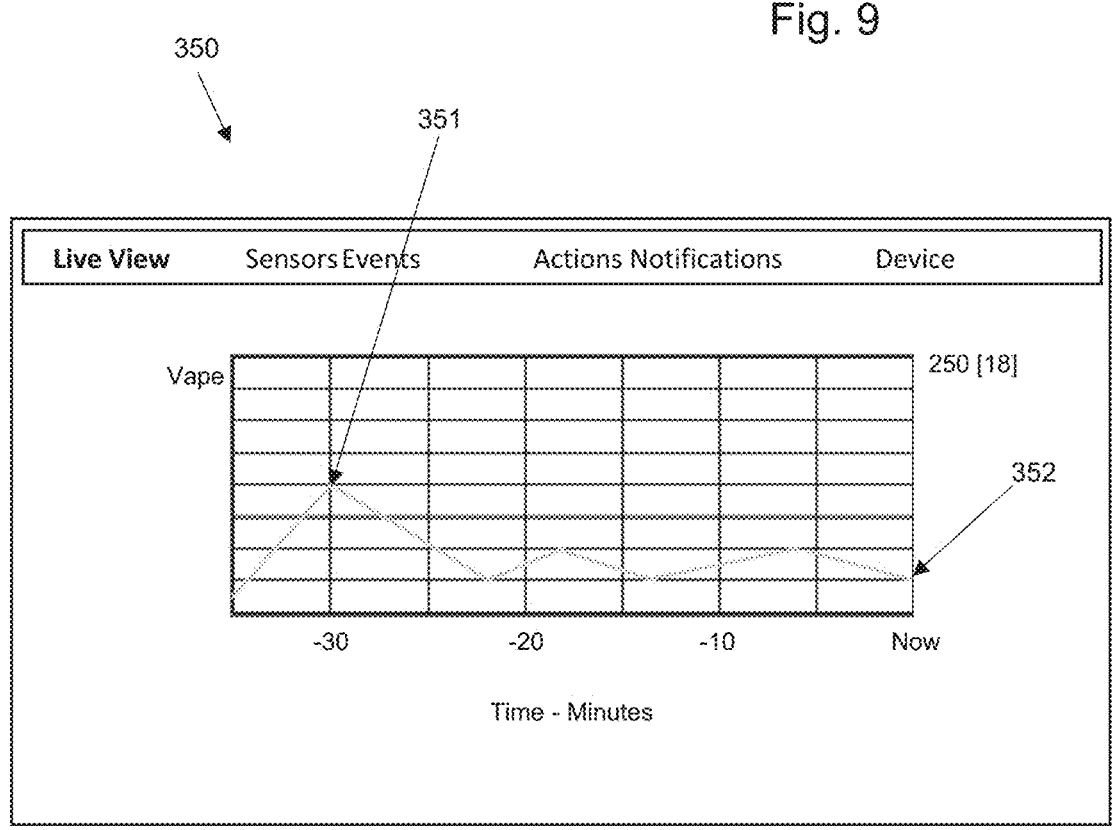
Figure 10:
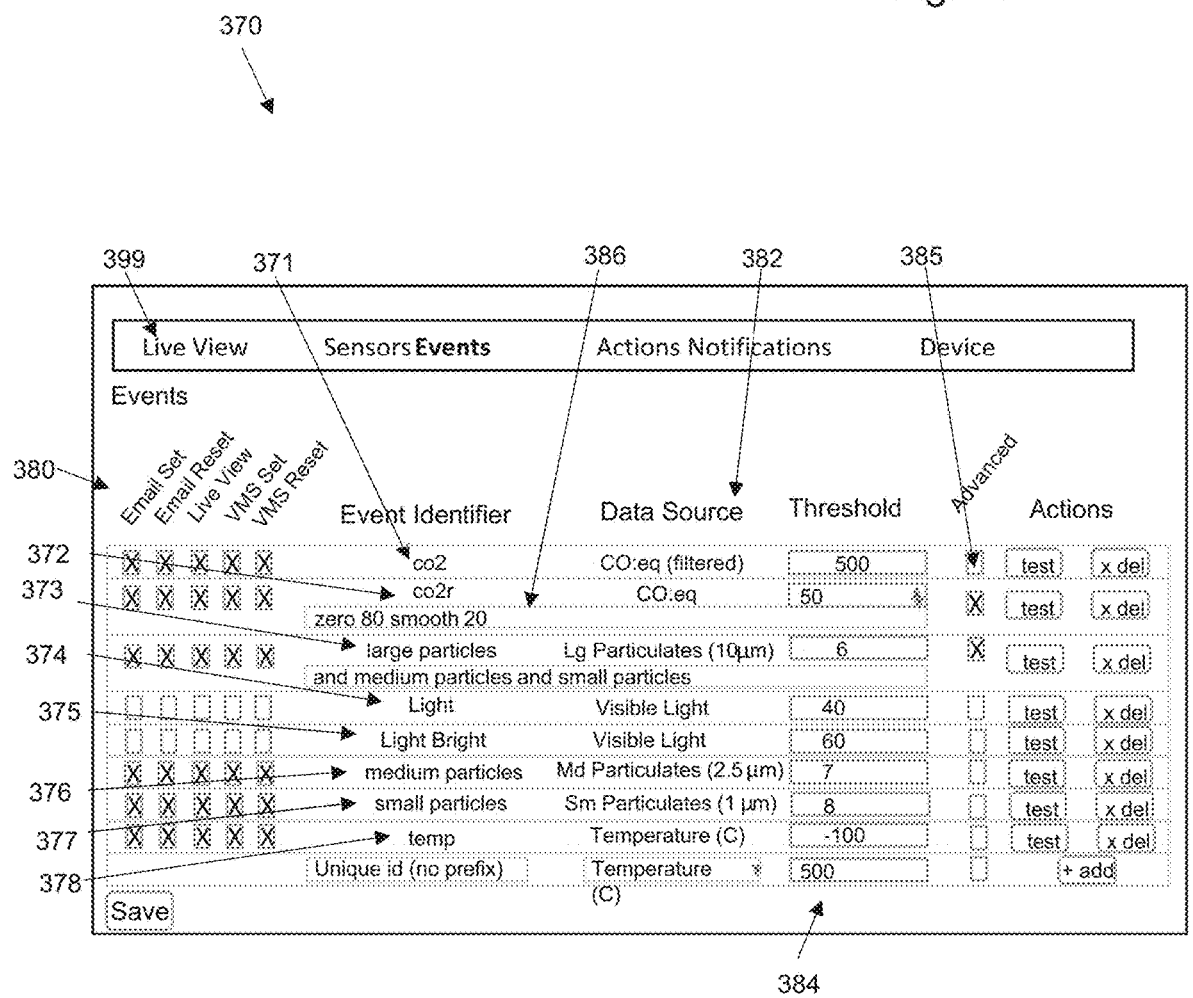

FIG. 9 shows an exemplary display 350 for graphically plotting measured levels over time. For example, the measured level of vaping at the current time 352 in display 350 is less than the level detected thirty minutes earlier as shown at 351. It will be appreciated that multiple sensors can be plotted on a single graph. FIG. 10 shows an exemplary display 370 for event configuration in accordance with the present disclosure, including a banner 399 permitting a user to select displays such as Live View, Sensors, Events, Actions, Notifications and Device. As shown therein, various events (e.g., 371-378) can be listed in successive rows, and a set 380 of selection boxes can be provided to denote appropriate actions to be taken if an event occurs, such as a measurement from one of the sensors of the sensor device exceeding a pre-set level. The pre-set or pre-established level can be input by a user of the event configuration interface 370. The primary data source (e.g., sensor) can be identified as at 382, and the threshold for the given event can be identified as at 384. In various embodiments, an "advanced" mode can be selected as at 385 in order to open a second line related to the event (e.g., 386) for a control script to be entered, for example. The control scripts can be powerful human-readable entries that enhance operation by providing for generation of events based on combinations of threshold crossings for both the primary sensors and one or several secondary sensors, for example, where each sensor has a separate threshold value. These can be combined with AND and/or OR logical operations, for example. The control scripts can further provide for time factors where the duration of the threshold crossing required for an alert may be explicitly defined. The control scripts can further be provided for defining both high pass (zero) and low pass (smooth) filters, which may have varying frequency and number of poles. For example, smooth 420 may define a low pass filter with a frequency of 20 and having four poles. This arrangement allows the application of tailored bandpass filters that are effective in extracting the desired value from very noisy raw data, for example.

As examples of the above, the device can be set to issue a detected event communication when the received monitoring data from just one of the group of sensors exceeds a pre-established threshold for that sensor. The device can issue a detected event communication when the threshold is exceeded at a specific time, or over a set period of time. The device can further issue a detected event communication when the threshold for a sub-group such as two or more sensors is exceeded, or when the threshold for only one sensor is exceeded while no other threshold for any other sensor has been exceeded.

FIGS. 11 through 16 and 22 show additional exemplary screen shots in accordance with aspects of the present disclosure. For example, FIG. 11 shows a screen shot 502 of an actions page, where an exemplary alert/detected event setting for a vandal event (e.g., a person tampering with the device) includes a selection 602 of the color red to be emitted by the LED device, a setting 603 of the device to blink once per second, and a setting 604 for the device to sound a siren.

Figure 12:

FIG. 12 shows a screen shot 506 of an alternative embodiment to that shown in FIG. 10 of an events page with advanced entry 605 unselected. FIG. 13 shows a screen shot 508 of an alternative embodiment to FIG. 10 of an events page with advanced entry 605 selected.

Figure 14:
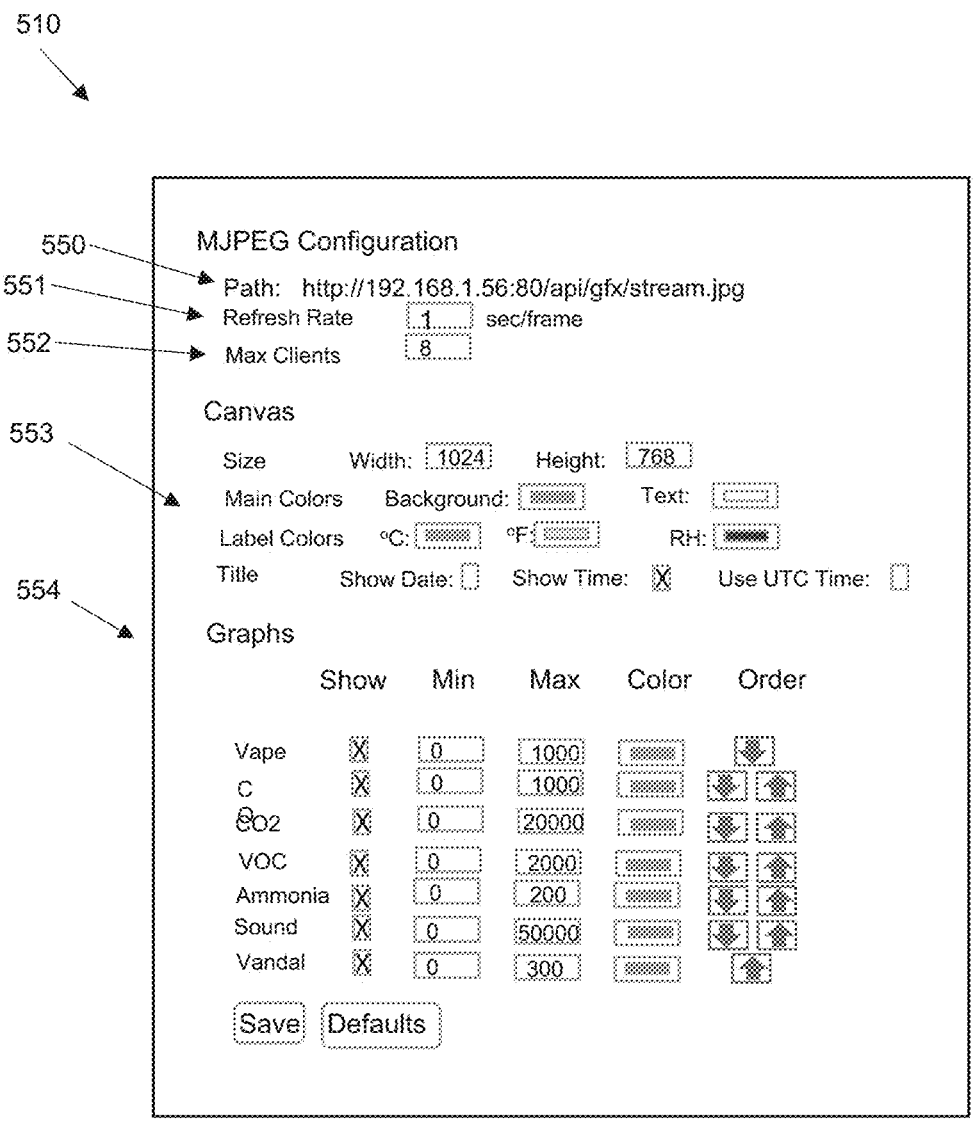

FIG. 14 shows a screen shot 510 of a live view configuration page, with the user able to configure the URL link as at 550, the refresh rate for images, for example, as at 551, the maximum number of clients as at 552, the display aspects as at 553 and the graphs for various deployed sensors as at 554. In this way, a sequence of digital images can be provided for display on a user interface of a communications device as described elsewhere herein, wherein the sequence of images conveys the received monitoring data as it changes over time. For example, the level of the listed substances at the time represented by the display 510 of FIG. 14 is likely to change over time, and these changed levels can be reflected in real time and/or near-real time.

Figure 16:
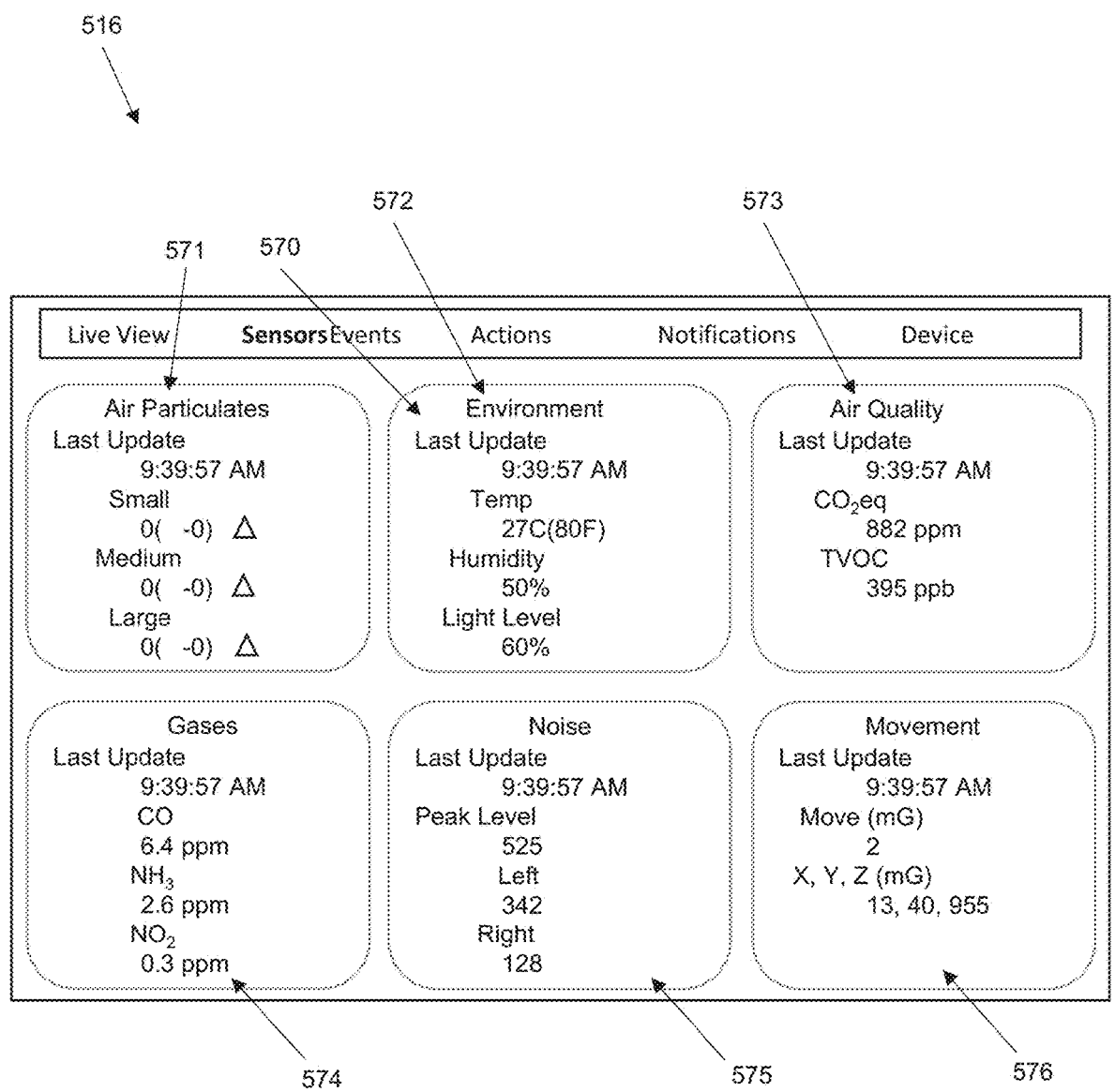

FIG. 15 shows an exemplary interface 514 in the form of a notifications page, permitting a user to set e-mail contents as at 560, SMTP settings as at 561 and VMS settings as at 562. FIG. 16 shows an exemplary interface 516 of a sensors page indicating a time of the last update (e.g., 570) and other measurements for air particulates 571, environment 572, air quality 573, gases 574, noise 575 and movement 576.

Figure 22:
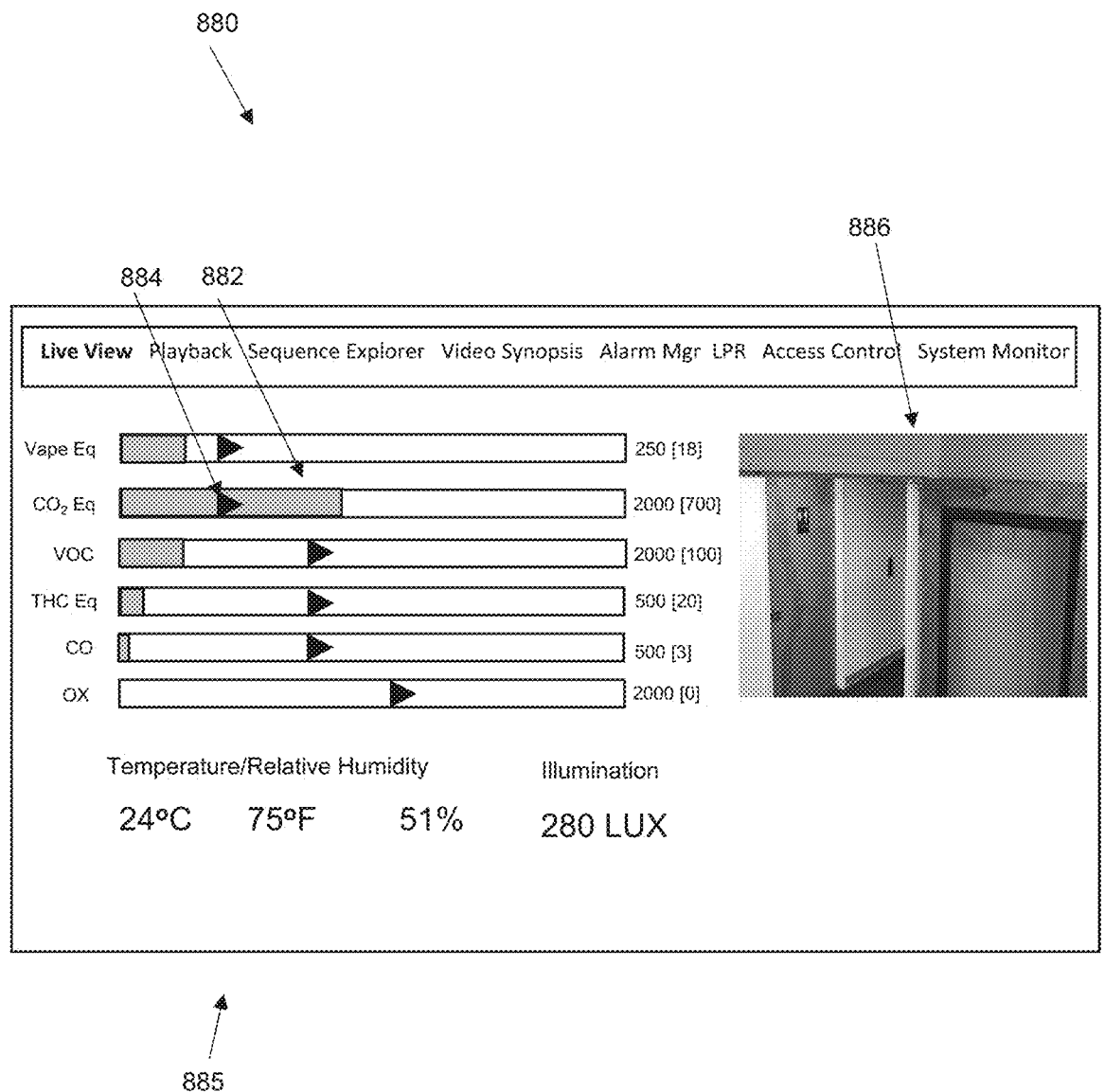
FIG. 22 is an exemplary screen shot in accordance with aspects of the present disclosure.

FIG. 22 shows an exemplary interface 880 of a user interface showing a live view of sensor readings 885 similar to FIG. 8. As shown in FIG. 22, the measurement 882 of carbon dioxide is shown to exceed the threshold 884, which has triggered the video recording by a video monitoring system that is monitoring a surveilled premises at or near where the sensor is located. In this example, the system has issued a detected event communication based on the received monitoring data exceeding the threshold for carbon dioxide such that the user interface shows the live video 886 being recorded alongside the sensor readings 885. In various embodiments, the sensor device may be located within an area such as a restroom, and the video camera of the video monitoring system is located outside of the restroom. In this example, the video-surveilled premises of the hallway outside of the restroom is proximate the location where the device is installed. By recording the video when, and after, the threshold measurement level has been exceeded, the system is likely to capture video of a potential perpetrator who may have caused the threshold measurement level to be exceeded. In various embodiments, audio is also recorded by the video camera(s).

Figure 23:
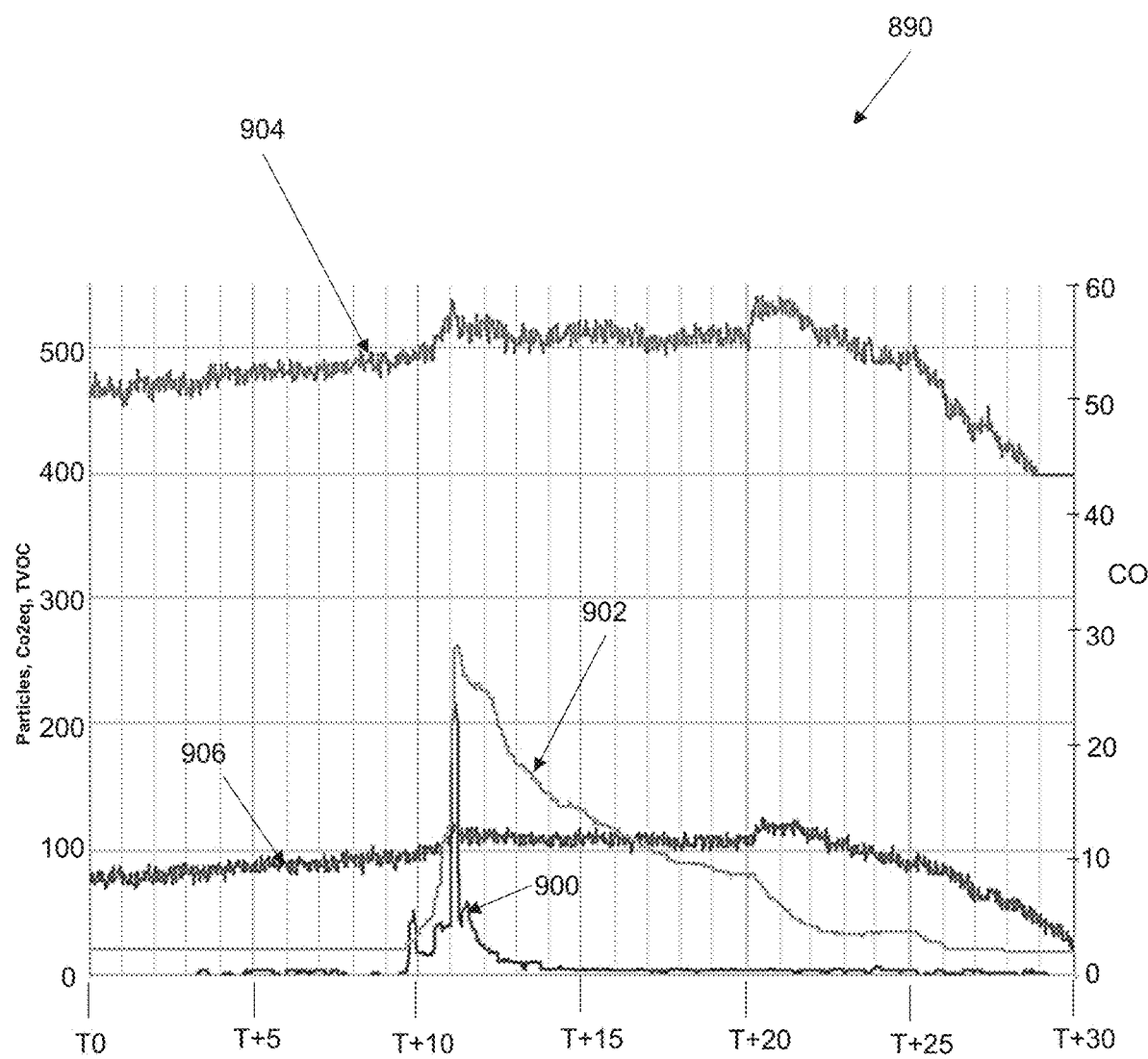
FIG. 23 is an exemplary plot of the sensor response for a heat-not-burn device.

FIG. 23 is a graph 890 showing sensor readings indicating a heat-not-burn device was utilized beginning at time T0 on a given day in a given location where a device according to the present disclosure was installed, such as a public restroom at a school, for example. In this example, the measurement of particles shown at 900 sharply increases over the particle threshold which may be set to 35 PPM in a profile for heat-not-burn activity, for example. At the same time, the measurement of CO shown at 902 also sharply increases over a threshold that may be set to 4 PPM in a profile for heat-not-burn activity, for example. Over the same period, we see CO2eq measurements shown at 904 and TVOC measurements shown at 906 increase as well; however, the increase is not over the exemplary thresholds of 550 PPM or 150 PPM from a profile for heat-not-burn activity, respectively. From the graph 890, one can see the sensors return to their pre-event values over time. FIG. 23 also demonstrates how these sensors behave with the introduction of fresh air as they return to levels below the pre-event state, such as between times T+20 and T+30, for example.

In exemplary embodiments, a profile for HNB device activity is established with a threshold for particles (e.g., 35 PPM), a threshold for CO (e.g., 4 PPM), a threshold for CO2 or CO2eq (e.g., 550 PPM) and a threshold for TVOC (e.g., 150 PPM). Additionally, the profile can be established so as to generate a detected event communication as described herein when one or more of the particles or CO measurement has exceeded its respective threshold at or over a specified period of time. For example, the profile for activity may require a particle measurement exceeding the 35 PPM threshold at a given time or may require a CO measurement exceeding the 4 PPM threshold at a given time. Many alternative profiles can be employed while still providing accurate HNB activity determinations. For example, the profile may require the particle measurement to exceed the 35 PPM threshold at a given time and then may require the CO measurement exceeding the 4 PPM threshold at some point in a given time gate or time window that encompasses the time when the particle measurement exceeding the 35 PPM threshold. The profile may further specify that the CO2eq threshold is not exceeded and/or that the TVOC threshold is not exceeded at the same time as the threshold(s) for particles and/or CO are exceeded. The profile for any given substance may be based on specific numerical concentrations, changes that are numerical, time-based or percentage-based and other factors. Further, different combinations of factors can be employed given the different substances being measured. For example, the profile for heat-not-burn activity may require the particle measurement to exceed its threshold twice such as at T+10 and T+11 in FIG. 3 in order to trigger a detected event communication. In such embodiments, the measurement value at the later time (i.e., T+11) may be required to be equal to or greater than the measurement value at the earlier time (i.e., T+10) as part of the profile for heat-not-burn activity. Such a profile may be based on the understanding that a user of a heat-not-burn device may have multiple exhalations during or after use of the heat-not-burn device and the system can therefore detect more than one exhalation as part of determining if the profile has been met. It will be appreciated that the heat-not-burn activity profile may specify that the first time and second time (e.g., T10 and T11) are within a defined period of time. The heat-not-burn activity profile may further specify that the measurement threshold is not exceeded at a different time (e.g., a third time) between the first time and second time. In this way, the system accommodates for scenarios where the exhalation cloud vapor dissipates into the environment and the sensor measurements return to below the defined threshold. In various embodiments, a moving average of measured background levels of a substance over a specified (e.g., programmable) period is determined and then subtracted from the current actual measurement in order to determine whether the measured substance meets or exceeds one or more thresholds.

As a further example for a heat-not-burn event detection, embodiments of the present disclosure can establish a profile that is met when particles are measured to exceed a designated threshold while carbon dioxide or CO2 equivalent are measured as not exceeding or being below a threshold. In other embodiments, a profile for a heat-not-burn event detection can be established and met when carbon monoxide exceeds a designated threshold while carbon dioxide or CO2 equivalent does not exceed a threshold. In still other embodiments, a profile for a heat-not-burn event detection can be established and met when particles exceed a designated threshold while the measurement of total volatile organic compounds (TVOC) does not exceed a threshold. In yet other embodiments, a profile for a heat-not-burn event detection can be established and met when carbon monoxide exceeds a designated threshold while TVOC does not exceed a threshold. In further embodiments, a profile for a heat-not-burn detection can be established and met when both particles and carbon monoxide exceed designated thresholds whereas either carbon dioxide, CO2 equivalent or TVOC does not exceed a threshold. In such embodiments, the particle detection sensor and CO sensor can be considered a sub-group of a group of sensors within a device, wherein exceeding the threshold for the sub-group provides an indication of heat-not-burn activity detection and can trigger a detected event notification as described elsewhere herein. In still further embodiments, a profile for a heat-not-burn detection can be established and met when one of particles or carbon monoxide exceeds a designated threshold whereas carbon dioxide (or CO2 equivalent) and TVOC do not exceed respective thresholds. It will be appreciated for all of the above examples that exceeding or not exceeding a threshold can be over a period of time or at a set time.

According to embodiments as described herein, a threshold for a profile can be a single measurement or a combination of measurements. For example, a CO2 threshold can be a single measurement for CO2 (or CO2 equivalent) and a TVOC threshold can be a single measurement for TVOCs. If either CO2 (or CO2 equivalent) or TVOC exceeds its respective threshold, the profile for a heat-not-burn event would not be met and therefore the measurement(s) would not be indicative of a heat-not-burn detection. As another example, a CO threshold can be a single threshold for CO measurements and a particle threshold can be a single threshold for particle measurements. In various embodiments, the system can sense that the particles measurement has exceeded the particle threshold. As a result, the system can operate according to a protocol such as may be provided via software instructions to then determine isolated measurements of CO over a time window or time gate that includes the time that the particle measurement was determined to exceed the particle threshold, as described elsewhere herein. In such embodiments, the system may effectively go back in time to prior measurements for CO and need not necessarily only assess real-time CO measurements going forward. If, for example, the system detects that CO exceeded a CO threshold during the time gate, this can provide confirmation according to a heat-not-burn profile that a heat-not-burn event has been detected. Further, if the profile requires that either or both of the CO2 or TVOC measurements do not exceed the respective thresholds for CO2 and/or TVOC, then the overall profile for a heat-not-burn event would be met and a suitable notification or other action can be generated as a result.

It will be appreciated that the event profile can be dynamic in order accommodate high levels of measured substances which may be normal in the environment the system is monitoring or for the period of time the system is monitoring. For instance, a device installed in an area where cooking is performed, would be expected to have higher levels of particles, CO2eq, TVOC and CO while cooking is performed. Embodiments of the present disclosure can remove "normal" background readings and only measure the delta increase due to the suspected event.

Removal of the average background levels can be accomplished by various mathematical processes. It will further be appreciated that the profiles for heat-not-burn activity, vaping activity and traditional cigarette or cigar smoking activity may all be different. Nevertheless, embodiments of the presently described device, system and method can accommodate detecting all such activities at the same or different times.

In various embodiments, upon determining that some portion or all of monitoring data received from one or more sensors indicates a matched substance profile and/or exceeded threshold, a detected event communication can be generated and sent to a communications device and/or the video monitoring system to begin recording the surveilled premises through one or more video cameras. Further, a detected event communication can be generated and sent to a device in the form of the video as it is recorded by the one or more video cameras. For example, a user interface associated with remote management system 124 may display a live view of selected sensors such that a user viewing the display knows the current measurements of those sensors, including the measurements of those sensors as they change over time. Such display can appear as in FIG. 8, where the measurements are constantly updated such as via MJPEG, H264 or other video compression technologies as described elsewhere herein. Upon one or more of the sensors exceeding a threshold, or some combination of sensor readings meeting an established profile, a detected event communication generated by the system can trigger the recording of the premises by the one or more cameras of the video monitoring system. At the same time, the recorded video can be a form of detected event communication that is generated and delivered to the user interface. In various embodiments, the recorded video is sent for display beginning at the time the detected event communication, or any detected event communication, is generated (e.g., at the time of determining an exceeded threshold or a profile match). As shown in FIG. 22, the recorded video can be displayed alongside the live view of the selected sensors.

It will be appreciated that any particular sensor can have multiple event entries with different settings. For instance, if a vape sensor detects a first level of vaping activity, a notification (i.e., detected event communication) may be sent to a video monitoring system (e.g., 122 in FIG. 7), whereas if the vape sensor detects a second level of vaping activity, a notification such as a text or e-mail may be sent to a person of authority via a user device 78.

It will be appreciated that the present disclosure contemplates several different methods of transmitting such alerts/detected event messages, including, but not limited to, external system native APIs, a REST interface, MQTT or wired connections. As described elsewhere herein, wired electrical bus connections may include CANBUS, MODBUS, RS-485, and others for wired connections to outside data sources and for direct signaling to external related systems such as HVAC controls, building management and automation systems and others. In various embodiments, a single LED is provided to display various system conditions and events, as described above in connection with device 111. The LED can display a wide range of colors and illumination patterns. These colors and illumination patterns are controlled by a separate subsystem which is in turned controlled by the central processor using the I2C bus. This arrangement allows the display of various colors and patterns without burdening the processor with their creation.

In various embodiments, the unit configuration is stored in a file that can be uploaded from and downloaded to the sensor device 10 via network 14. This file design can include a checksum to ensure against corruption and a double buffering mechanism to a complete download and check before the file is installed, for example. This buffering includes the ability keep the current version in memory during a download and to return to this last operational version if the download causes a malfunction. This file can include data and parameters for at least configuration of all sensors, logic for local alerting functions, algorithm weighting parameters and functions and date/time schedule(s).

Local rules can include connection of the local status LED 111 and the relays 53 to the outputs of the sensor data processing algorithms or with thresholds to native sensor values. In various embodiments, each rule consists of an input selection, threshold as applicable, output selection, schedule for applicability, duration of output action for each triggering event, and hold off time after a triggering event. The output of a rule can include an email or API push action with content including the source and source state that triggered the rule. Rules can be triggered on threshold crossing in a particular direction or be valid once a threshold is crossed in a particular direction. Schedules can be based on active days of week and active times during the day with one-minute resolution. Schedules can also include an organizational tag like "vacation" or "show" or a specific single date or date range. The API includes a parameter to set the mode of the unit to match one of these tags to activate the schedules with that tag.

In various embodiments, the presently disclosed system provides multiple user interfaces, accessible, for example, at a URL assigned to the unit (e.g., 550 in FIG. 14). It will be appreciated that there may be a hard-coded default URL and credentials may be provided that make it possible to configure basic settings from a browser operable via any suitable communications device (e.g., 78 in FIG. 7). Various pages of information can be provided via the user interface(s). For example, the "Live View" page provides information on the current state of the Halo device, much of it in graphical form. The Configuration page is used to set up the device, such as with the following readouts and settings, for example: Server IP Address, Server Port, Server User II), Server Password, User DHCP, Local IP Address, Local Port, Local User ID, Local Password, Allow Remote Firmware Upgrade [T/F], Enable Local Security [T/F]. Defaults are designed to allow local connection for initial configuration.

As described elsewhere herein, the functionality of the presently disclosed device and system can be primarily configured, controlled and accessed through an application programming interface (API), such as a Web Services REST API. In various embodiments, the presently disclosed system provides for inbuilt integration with specific external systems, such as a video management system 122 through a plug-in driver. Other external systems are directly interfaced with other plugin drivers. The MQTT publish and subscribe message system can be employed as another "no programming" mechanism for event delivery. MQTT is a machine-to-machine (M2M)/"Internet of Things" connectivity protocol.

In various embodiments, the presently disclosed device and system can be connected to a cloud-based program where the generation and dissemination of alerts/detected events communications is performed. A multitude of devices according to the present disclosure can be displayed on a map or building location to provide their absolute GPS location or relative location on a building floor plan. The results from these multitude of devices can be used to generate heat maps of problematic areas and be programmed to generate alerts/detected event communications based upon the density of the heat map rather than just the sensors values exceeding an individual programmable limit. It will be appreciated that the sensor device can be securely configured and monitored via a cloud-based portal, which may be hosted by a third party, for example. Connections to the portal can be established via HTTPS. Administrators can edit device settings, define sensor thresholds and create and edit event rules to trigger other applications and devices. Account settings control groups, individual users and permissions to define who has access to the portal account. Multiple logins can be added to a single account, for example. An account can contain maps for multiple buildings or locations, so all devices can be managed through a single login.

In embodiments incorporating cloud-based operations and other embodiments, it will be appreciated that the processor need not be placed or secured within the housing of the device. For example, raw sensor data collected via the device and/or system as described herein can be transmitted to the cloud-based portal and the processing and subsequent actions can thereby be performed remotely.

Thus, regardless of the location of the processor, the system can operate so as to receive data from the one or more sensors, process the data such as by averaging, reducing noise, filtering, performing FFT, integration, derivatives and other analysis, combine the data among multiple sensors as appropriate, assess whether applied thresholds have been met, and if any thresholds have been met, trigger appropriate actions, such as alerts, communications and other actions as described herein. The system can further learn from and improve operations via a learning and/or neural network as described elsewhere herein. The system can also operate to time and schedule alerts, and store sensor data and alerts in a database as described herein. Such processing operations can occur in the sensor driver software and circuitry directly associated with each sensor, in the local microprocessor within the housing, in a local gateway device that serves multiple sensors devices, in the "cloud" server that supports a larger number of devices and/or in the user's application (e.g., mobile communications device application) that displays the data.

In various embodiments, the portal can provide a map interface where each sensor within the sensor device is displayed on a floorplan that shows the physical location of each sensor device. Users can then click on an icon for any device to interact with the data from that specific device.

Users can monitor each sensor individually or collectively via a dashboard interface that displays the real-time data flow for each of the unique sensors for each managed device, in the form of data tables, graphical charts and graphs. The dashboard can display event indicators if defined thresholds are triggered on a sensor. The portal can send generate and send text, email and push notification to mobile devices when a device is triggered. Users can generate reports based on current or historic data that is saved in the portal, Concentration maps can be exported to review problematic areas. According to various embodiments, a cloud-based portal can also perform deeper real-time analysis and alert generation based on addition available computational power and the possibility of incorporating data from additional sensor units located in the same general area. For example, the migration of a gas concentration or unusual sound from one area to another can be detected and used to generate a specific alert/detected event communication.

Figure 17:
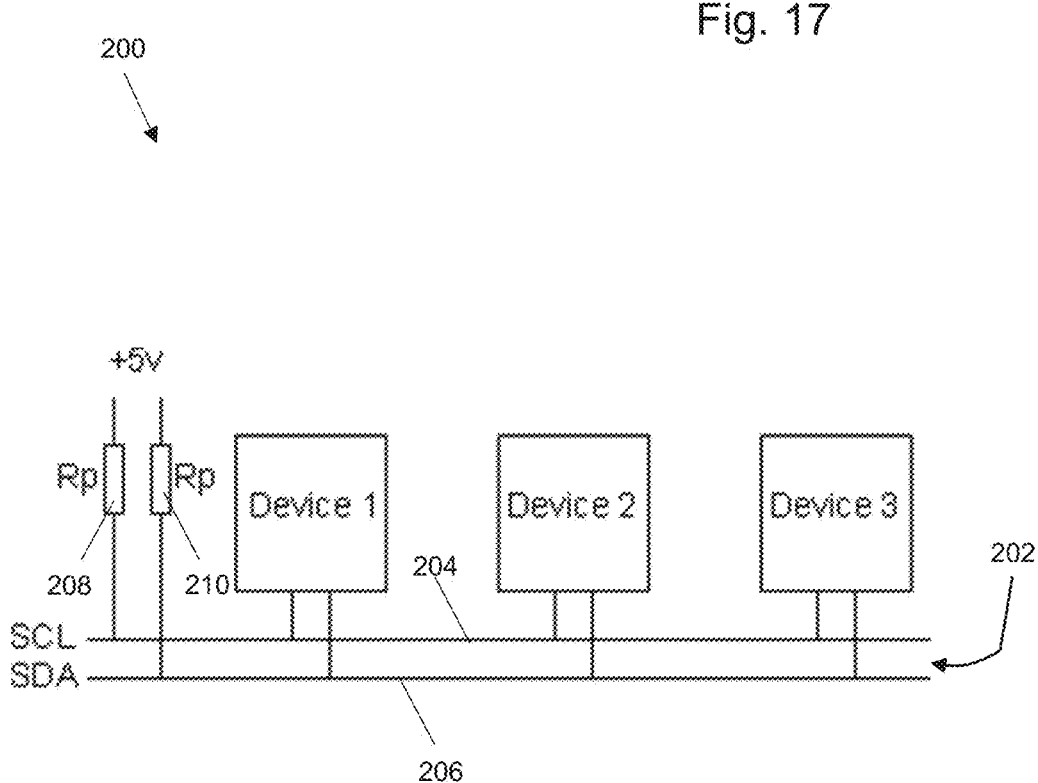
FIG. 17 illustrates an example partial circuit diagram including a set of pull-up resistors for an I2C bus.

Referring to FIG. 17 and with regard to I2C Bus Communication 200, an I2C bus 202 passes data between the microcontroller and several of the sensors and output subsystems in accordance with one or more implementations. The physical I2C bus topology can include two dedicated wires (circuits): SCL 204 and SDA 206. SCL 204 is the clock line and used to synchronize data transfers over the I2C bus. SDA 206 is the data line. The SCL, 204 and SDA 206 lines are connected to all devices on the I2C bus. Both SCL 204 and SDA 206 lines are "open drain" drivers, in that the chip drives its output low, but not high. For the line to be able to go high, the design provides pull-up resistors to the 5v supply. For example, a resistor 208 is provided from the SCL, line to the 5v line and another resistor 210 from the SDA line to the 5v line. Accordingly, the implementation shown in FIG. 17 includes a set of pull-up resistors 208, 210 for the I2C bus 202, not for each device. The values of these resistors can be 220 ohms, which provides a good balance between bus speed and power consumption. Devices one through three on the I2C bus can be configured as masters or slaves. For example, the master device drives the SCL 204 clock line, and slaves respond to the master. In one or more implementations and unlike a master device, a slave cannot initiate a transfer over the I2C bus 202. In one or more implementations, multiple slaves can be provided on the I2C bus 202 with one master. Both master and slave devices can transfer data over the I2C bus 202, which is typically controlled by the master. Moreover, in one or more implementations, the microcontroller can be the master.

In an example operation, when the master (e.g., the controller) talks to a slave (the light sensor 109, for example) the master begins by issuing a start sequence on the I2C bus 202. A start sequence can be one of two special sequences defined for the I2C bus 202, the other being the stop sequence. In one or more implementations, the start sequence and stop sequence are special in that these are the only places where the SDA 206 (data line) is allowed to change while the SCL 204 (clock line) is high. When data is being transferred, SDA remains stable and does not change while SCL is high. The start and stop sequences mark the beginning and end of a transaction with the slave device.

Serial Peripheral interface (SPI) is a synchronous serial data protocol used by microcontrollers for communicating with one or more peripheral devices quickly over short distances. It can also be used for communication between two microcontrollers. With an SPI connection there is always one master device (usually a microcontroller) which controls the peripheral devices. Typically, there are three lines common to all the devices: [0099] MIS( ) (Master In Slave Out)—The Slave line for sending data to the master, [0100] MOSI (Master Out Slave In)—The Master line for sending data to the peripherals, [0101] SCK (Serial Clock)—The clock pulses which synchronize data transmission are generated by the master and one line specific for every device: [0102] SS (Slave Select)—the pin on each device that the master can use to enable and disable specific devices.

When a device's Slave Select pin is low, it communicates with the master. When the pin is high, it ignores the master. This accommodates multiple SPI devices sharing the same MISO, MOSI, and CLK lines. The SPI interface is more complex than the I2C, but capable of higher speed data transfer resulting in its application to the audio data.

Audible Alerting

In various embodiments, the sensor of the present disclosure provides alerts on a large spectrum of possible conditions with each alert configurable in almost unlimited ways. This flexibility makes it useful to provide a more nuanced local alerting mechanism than the single buzzer in a simple smoke alarm. Because the sensor package need not be employed for life safety applications, any audio alert provided does not need to be overly intrusive.

Figure 18:
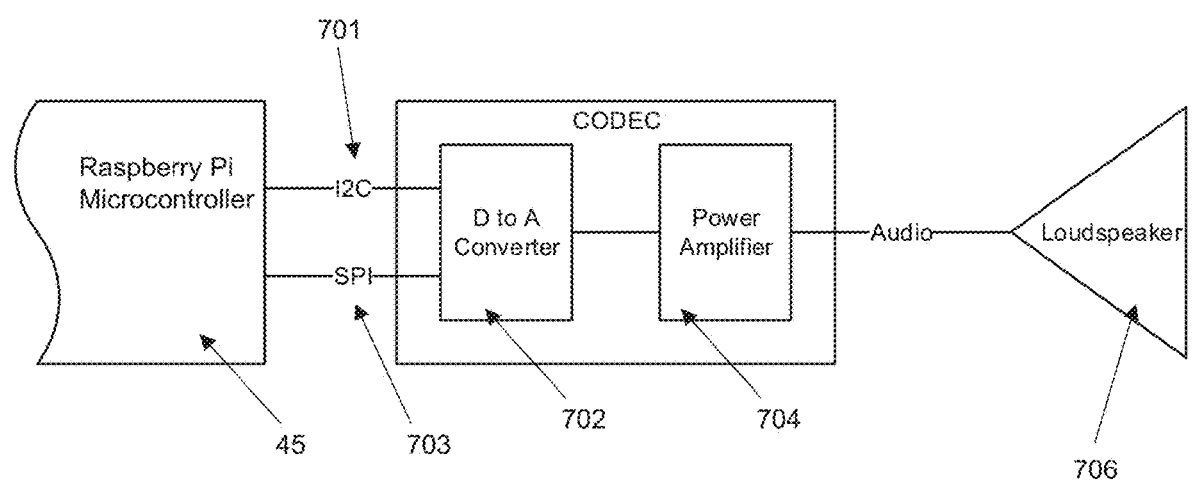
FIG. 18 is a schematic diagram of an audible alerting component in accordance with embodiments of the present disclosure.

FIG. 18 depicts a D to A converter 702, power amplifier 704 and loudspeaker 706 that may be utilized in various embodiments of the sensor. The volume of the audio output may be adjusted by a register in the CODEC controlled using the I2C bus 701 while a stream of data representing the desired audio output is delivered through the I2S bus 703 from the microcontroller 45, for example. The power amplifier provides sufficient voltage and current to drive the loudspeaker to a useful sound level. The audio output can also be connected to an external amplifier or sound system for greater sound level or wider distribution. The waveforms representing the desired alerting sounds can generated directly by a program, derived from files of pre-recorded sounds stored in the sensor memory, or delivered to the sensor over its network connection. Various sounds can be made available for various alerts. These sounds can be tone patterns like sirens or bells, or human speech.

The configuration utility of the sensor allows associating any one or more of these sounds with any desired alert condition. The sound may be arranged to play once, a number of times, or play continually as long at the alert is in effect. The sensor can also utilize other forms of audible alerts including, but not limited to electrical buzzers and bells. In various embodiments, the firmware implements a learning mode where the algorithm or other self-learning topology is "programmed" by learning what the sensor readings look like for a normal room or location. In various embodiments, this setup is all that is required. Anything that does not "seem" like normal conditions is an alert.

Advanced Conditions

It will be appreciated that the usability of the sensor under real world conditions is a very important attribute of the embodiments of the design disclosed herein. The values and changes of interest in the data provided by the various sensors is often masked by random changes that occur on a different time scale and obscured by lack of selectivity of the physical sensor channel s.

In various embodiments, Advanced Conditions of the present disclosure allow for filtering and combining values numerically, logically, and with respect to time. The purpose of the filtering, combining and timing is to extract reliable alerting indications from the raw data captured by the sensors.

Some sensor data exhibits slow baseline drift that may eventually cause a preset threshold to be crossed in the absence of a true physical event. A high pass filter function can be provided that can be used to reduce or eliminate baseline drift and other undesired low frequency data components. This filter can be optimized by selecting the desired number of poles from 1 to 4, and the time constant in seconds, for example.

Some sensor data exhibits high frequency noise that is not representative of physical events of interest but may cross a preset threshold. A low pass filter function can be provided according to the present disclosure that can be used to reduce or eliminate high frequency noise and spikes in the raw data. This filter can be optimized by selecting the desired number of poles from 1 to 4, and the time constant in seconds, for example. In various embodiments, the high and low pass filters may be used together to create a bandpass filter with optimized response.

When physical events excite more than one sensor channel, a profile can be implemented by combining the values from the sensors in question. Channels can be combined either logically, and/or arithmetically (+, −). If a given type of detected event is seen to affect two sensor channels, then better discrimination may be achieved by combining thresholds for these two sensors logically. For example, channel A>1000 and channel B>2000 provides better discrimination than either threshold process alone. The operation of the threshold applied to these raw or calculated values may be modified by including fixed numeric values (constants) in the combinational equations. For example, Sensor A+1500 is a valid computation.

When data from more than one sensor channel are to be combined arithmetically or plotted together for comparison, it can be useful to have these data in the same general numerical range. This can be accomplished by applying a scaling function that maps the range and Y intercept of a given sensor to any other desired range and Y intercept. The scaling function may be used to invert the range of values of any sensor.

Time related functions can also be used to further discriminate against spurious responses. For example, if a sensor is in a public school that operates Monday through Friday only, with no weekend activities, the device and system may not be set to operate on Saturdays and Sundays, or on particular times during the week. A "Rate" function can be employed to suppress the unchanging component of a value and extract the rate of change, which can be a useful criterion in some circumstances. For example, if there is a fire and the temperature rises drastically within a few minutes, the rate of temperature change may be considered to initiate a detected event communication. A "Require" function can be employed to establish that a given state must be true for at least a specified time period. A "Hold" function can be employed to hold the set state of a comparison for a specified time past its natural reset point. All resets are affected. An "Extend" function can be employed to hold the set state for at least the specified time. Long set states are unaffected. This has the effect of filtering out short reset periods. The above-described embodiments of the present disclosure may be implemented in accordance with or in conjunction with one or more of a variety of different types of systems, such as, but not limited to, those described elsewhere herein.

The present disclosure contemplates a variety of different systems each having one or more of a plurality of different features, attributes, or characteristics. A "system" as used herein can refer, for example, to various configurations of: (a) one or more sensor devices; (b) one or more sensor devices and one or more external computing devices; (c) one or more sensor devices communicating via one or more networks; (d) one or more sensor devices and one or more external computing devices communicating via one or more networks; and (e) one or more personal computing devices, such as desktop computers, laptop computers, tablet computers, personal digital assistants, mobile phones, and other mobile computing devices. A system as used herein can also include one or more sensor units and a gateway device designed to capture and amalgamate the information from connected sensor units and transmit this information over the more general or public network with increased efficiency and security. This gateway can also act as a management tool and a sensor health monitor for a group of sensor units, for example.

In certain embodiments in which the system includes a personal computing device in combination with a sensor device, the computing device is any suitable computing device (such as a server) that includes at least one processor and at least one memory device or data storage device. As further described herein, the personal computing device includes at least one processor configured to transmit and receive data or signals representing events, messages, commands, or any other suitable information between the personal computing device and the sensor device. The processor of the personal computing device is configured to execute the events, messages, or commands represented by such data or signals in conjunction with the operation of the personal computing device. Moreover, the processor of the sensor device is configured to transmit and receive data or signals representing events, messages, commands, or any other suitable information between the sensor device and the personal computing device. The processor of the sensor device host is configured to execute the events, messages, or commands represented by such data or signals in conjunction with the operation of the sensor device.

In operation, the sensor device 10 can be installed and can require a wired network connection (Ethernet) which includes standard 802.3af PoE power. In various embodiments, this connection should not be longer than 300 feet (100 M). The sensor device 10 is preferably located on a ceiling or high on a wall to limit casual access. Further, the device 10 should be in an area relatively free of air currents and areas with significant background noise or vibration. The network cable is plugged into a jack such as an RJ-45 jack on the face 30 of the case 15. Programming provided with the sensor device 10 can be employed to find the unit being installed on the network and change the unit's network configuration in accordance with the facility network plan.

In embodiments in which the system includes a personal computing device configured to communicate with a sensor device 10 through a data network (e.g., 14 in FIG. 7), the data network is a local area network (LAN), a wide area network (WAN), a public network such as the Internet, or a private network. The sensor device 10 and the personal computing device (e.g., 78) are configured to connect to the data network or remote communications link in any suitable manner. In various embodiments, such a connection is accomplished via: a conventional phone line or other data transmission line, a digital subscriber line (DSL), a T-1 line, a coaxial cable, a fiber optic cable, a wireless or wired routing device, a mobile communications network connection (such as a cellular network or mobile Internet network), or any other suitable medium.

In various embodiments, the operation of the alerting light and the illumination sensor can be timed so that they do not interact. Further, the sensor package can be self-tested through deliberate interaction of pairs of sensors such as loudspeaker and microphones or light and illumination sensor. In addition, the system as presently disclosed can internally store historical data from all sensors for the purposes of automatic or manual analysis to improve sensor unit operation as well as to troubleshoot the unit or the installation, and to have the sensor unit replay such data for demonstrations. Stored data can be easily retrieved over the network connection or by physical removal of a memory device and can further be erased remotely when desired.

It will be appreciated that any combination of one or more computer readable media may be utilized. The computer readable media may be a computer readable signal medium or a computer readable storage medium. A computer readable storage medium may be, for example, but not limited to, an electronic, magnetic, optical, electromagnetic, or semiconductor system, apparatus, or device, or any suitable combination of the foregoing, including a portable computer diskette, a hard disk, a random access memory (RAM), a read-only memory (ROM), an erasable programmable read-only memory (EPROM or Flash memory), an appropriate optical fiber with a repeater, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device. Program code embodied on a computer readable signal medium may be transmitted using any appropriate medium, including but not limited to wireless, wireline, optical fiber cable, RF, etc., or any suitable combination of the foregoing.

As will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, microcode, etc.) or combining software and hardware implementation that may all generally be referred to herein as a "circuit," "module," "component," or "system." Furthermore, aspects of the present disclosure may take the form of a computer program product embodied in one or more computer readable media having computer readable program code embodied thereon.

It will be appreciated that all of the disclosed methods and procedures herein can be implemented using one or more computer programs or components. These components may be provided as a series of computer instructions on any conventional computer-readable medium, including RAM, SATA DOM, or other storage media. The instructions may be configured to be executed by one or more processors which, when executing the series of computer instructions, performs or facilitates the performance of all or part of the disclosed methods and procedures.

Unless otherwise stated, devices or components of the present disclosure that are in communication with each other do not need to be in continuous communication with each other. Further, devices or components in communication with other devices or components can communicate directly or indirectly through one or more intermediate devices, components or other intermediaries. Further, descriptions of embodiments of the present disclosure herein wherein several devices and/or components are described as being in communication with one another does not imply that all such components are required, or that each of the disclosed components must communicate with every other component. In addition, while algorithms, process steps and/or method steps may be described in a sequential order, such approaches can be configured to work in different orders. In other words, any ordering of steps described herein does not, standing alone, dictate that the steps be performed in that order. The steps associated with methods and/or processes as described herein can be performed in any order practical. Additionally, some steps can be performed simultaneously or substantially simultaneously despite being described or implied as occurring non-simultaneously.

It will be appreciated that algorithms, method steps and process steps described herein can be implemented by appropriately programmed computers and computing devices, for example. In this regard, a processor (e.g., a microprocessor or controller device) receives instructions from a memory or like storage device that contains and/or stores the instructions, and the processor executes those instructions, thereby performing a process defined by those instructions. Furthermore, aspects of the present disclosure may take the form of a computer program product embodied in one or more computer readable media having computer readable program code embodied thereon.

Computer program code for carrying out operations for aspects of the present disclosure may be written in any combination of one or more programming languages, including an object oriented programming language such as Java, Scala, Smalltalk, Eiffel, JADE, Emerald, C++, C#, VB.NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on a user's computer, partly on a user's computer, as a stand-alone software package, partly on a user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS). It will be appreciated that the computer code may also be implemented using an RTOS (real time operating system) together with appropriate application code to provide a more timely response capability.

Where databases are described in the present disclosure, it will be appreciated that alternative database structures to those described, as well as other memory structures besides databases may be readily employed. The drawing figure representations and accompanying descriptions of any exemplary databases presented herein are illustrative and not restrictive arrangements for stored representations of data. Further, any exemplary entries of tables, charts, graphs and parameter data represent example information only, and, despite any depiction of the databases as tables, other formats (including relational databases, object-based models and/or distributed databases) can be used to store, process and otherwise manipulate the data types described herein. Electronic storage can be local or remote storage, as will be understood to those skilled in the art. Appropriate encryption and other security methodologies can also be employed by the system of the present disclosure, as will be understood to one of ordinary skill in the art.

It will thus be appreciated that embodiments of the present disclosure provide a system, method and device employing a group of sensors optionally secured within a housing, wherein the group of sensors can comprise a carbon monoxide detection sensor, a carbon dioxide (equivalent) sensor, a particle detection sensor and a volatile organic compound sensor; wherein a profile for heat-not-burn activity is generated and can include a threshold for measurements from one or more of the group of sensors, wherein the threshold for any given measurement can be numerical, time-based and/or percentage based. The system, method and device can further receive monitoring data from each of the group of sensors; and upon determining that at least a portion of the received monitoring data is indicative of an exceeded threshold for one or more of the group of sensors from the profile for heat-not-burn activity, generate a detected event communication for the heat-not-burn activity.

The invention claimed is:

1. A device, comprising:
   at least one sensor;
   a processor; and
   a memory storing instructions that, when executed by the processor, cause the processor to:
      establish a profile for heat-not-burn device activity, wherein the profile comprises a threshold for a measurement from the at least one sensor;
      receive monitoring data from the at least one sensor at a first value at a first time and at a second value at a second time later than the first time; and
      upon determining that the first value and the second value exceed the threshold from the profile for heat-not-burn device activity, generate a detected event communication for the heat-not-burn device activity.

2. The device of claim 1, wherein the second value is equal to or greater than the first value.

3. The device of claim 1, wherein the second time is within a defined period of time after the first time.

4. The device of claim 1, wherein the instructions further cause the processor to receive monitoring data from the first one of the group of sensors at a third value at a third time that is between the first time and the second time, and wherein the third value is below the threshold from the profile.

5. The device of claim 1, wherein the at least one sensor is a carbon monoxide sensor.

6. The device of claim 1, wherein the at least one sensor is a particle detection sensor.

7. The device of claim 1, wherein the at least one sensor comprises a carbon monoxide sensor and a particle detection sensor, and wherein the profile comprises a threshold for a carbon monoxide measurement and a particle detection measurement.

8. The device of claim 7, wherein the instructions farther comprise instructions that when executed by the processor cause the processor to:
   receive monitoring data from the particle detection sensor at the first value at the first time and at the second value at the second time later than the first time; and
   receive monitoring data from the carbon monoxide sensor at a third value at the first time and at a fourth value at the second time;
   determine that the second value meets or exceeds the first value; and
   determine that the fourth value meets or exceeds the third value.

9. A computer-implemented method, comprising
   establishing a profile for heat-not-burn device activity, wherein the profile comprises a threshold for a measurement from the at least one sensor;
   receiving monitoring data from the at least one sensor at a first value at a first time and at a second value at a second time later than the first time; and
   upon determining that the first value and the second value exceed the threshold from the profile for heat-not-burn device activity and that the second value is equal to or greater than the first value, generating a detected event communication for the heat-not-burn device activity.

10. The method of claim 9, wherein the at least one sensor comprises a carbon monoxide sensor and a particle detection sensor, and wherein the profile comprises a threshold for a carbon monoxide measurement and a particle detection measurement.

11. The method of claim 10, wherein receiving monitoring data comprises receiving monitoring data from the particle detection sensor at the first value at the first time and at the second value at the second time later than the first time, and receiving monitoring data from the carbon monoxide sensor at a third value at the first time and at a fourth value at the second time; and
   wherein the method further comprises determining that the second value meets or exceeds the first value, and that the fourth value meets or exceeds the third value prior to generating the detected event communication.

12. A device for detecting heat-not-burn device activity and human e-cigarette exhalation activity, comprising:
   a group of sensors comprising a carbon monoxide detection sensor and a particle detection sensor;
   a processor; and
   a memory storing instructions that, when executed by the processor, cause the processor to:
      establish a profile for heat-not-burn device activity, wherein the profile comprises a threshold for a measurement from at least one of the group of sensors;
      establish a vaping profile for human e-cigarette exhalation activity, wherein the vaping profile specifies a threshold concentration of particles;
      receive monitoring data from the group of sensors;
      upon determining that at least a portion of the received monitoring data indicates that the threshold from the profile for heat-not-burn device activity has been exceeded, generate a detected heat-not-burn event communication; and
      upon determining that at least a portion of the received monitoring data indicates that the threshold concentration from the vaping profile has been exceeded, generate a detected vaping event communication.

13. The device of claim 12, wherein the vaping profile is different from the heat-not-burn device activity profile.

14. The device of claim 12, wherein the instructions further cause the processor to receive monitoring data from the at least one of the group of sensors at a first value at a first time and at a second value at a second time later than the first time; and upon determining that the first value and the second value exceed the threshold from the profile for heat-not-burn device activity, generate the detected event communication for the heat-not-burn device activity.

15. The device of claim 14, wherein the instructions further cause the processor to generate the detected event communication for the heat-not-burn device activity upon determining that the second value is equal to or greater than the first value.

16. The device of claim 14, wherein the second time is within a defined period of time after the first time.

17. The device of claim 14, wherein the instructions further cause the processor to receive monitoring data from the first one of the group of sensors at a third value at a third time that is between the first time and the second time, and wherein the detected event communication is generated if the third value is below the threshold from the profile.

18. The device of claim 12, wherein the profile for heat-not-burn device activity comprises a threshold for a carbon monoxide measurement and a particle detection measurement.

19. The device of claim 12, further comprising a camera, wherein the detected heat-not-burn event communication comprises a video recording from the camera.

20. The device of claim 19, wherein the instructions further cause the processor to transmit the video recording for display on a user interface upon the detected heat-not-burn event communication being generated.

\* \* \* \* \*